US012653795B1

(12) United States Patent
Tabuteau

(10) Patent No.: US 12,653,795 B1

(45) Date of Patent: Jun. 16, 2026

(54) BUPROPION AS A MODULATOR OF DRUG ACTIVITY

(71) Applicant: ANTECIP BIOVENTURES II LLC, New York, NY (US)

(72) Inventor: Herriot Tabuteau, New York, NY (US)

(73) Assignee: ANTECIP BIOVENTURES II LLC, New York, NY (US)

( * ) Notice: Subject to any disclaimer, the term of this patent is extended or adjusted under 35 U.S.C. 154(b) by 0 days.

(21) Appl. No.: 19/255,952

(22) Filed: Jun. 30, 2025

Related U.S. Application Data

(63) Continuation of application No. 18/529,217, filed on Dec. 5, 2023, now abandoned, which is a continuation of application No. PCT/US2023/081292, filed on Nov. 28, 2023.

(60) Provisional application No. 63/589,525, filed on Oct. 11, 2023, provisional application No. 63/589,325, filed on Oct. 11, 2023, provisional application No. 63/385,205, filed on Nov. 28, 2022.

(51) Int. Cl.

| | |
|---|---|
| ***A61K 47/69*** | (2017.01) |
| ***A61K 9/20*** | (2006.01) |
| ***A61K 9/24*** | (2006.01) |
| ***A61K 31/137*** | (2006.01) |
| ***A61K 31/485*** | (2006.01) |
| ***A61P 25/28*** | (2006.01) |

(52) U.S. Cl.
CPC .......... *A61K 31/137* (2013.01); *A61K 9/2009* (2013.01); *A61K 9/2013* (2013.01); *A61K 9/2027* (2013.01); *A61K 9/2054* (2013.01); *A61K 9/209* (2013.01); *A61K 31/485* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 5,358,970 | A | 10/1994 | Ruff et al. |
| 5,731,000 | A | 3/1998 | Ruff et al. |
| 5,763,493 | A | 6/1998 | Ruff et al. |
| 6,306,436 | B1 | 10/2001 | Chungi et al. |
| 6,780,871 | B2 | 8/2004 | Glick et al. |
| 8,088,786 | B2 | 1/2012 | Mckinney et al. |
| 8,569,328 | B1 | 10/2013 | Tabuteau |
| 9,168,234 | B2 | 10/2015 | Tabuteau |
| 9,198,905 | B2 | 12/2015 | Tabuteau |
| 9,205,083 | B2 | 12/2015 | Tabuteau |
| 9,238,032 | B2 | 1/2016 | Tabuteau |
| 9,278,095 | B2 | 3/2016 | Tabuteau |
| 9,314,462 | B2 | 4/2016 | Tabuteau |
| 9,370,513 | B2 | 6/2016 | Tabuteau |
| 9,375,429 | B2 | 6/2016 | Tabuteau |
| 9,402,843 | B2 | 8/2016 | Tabuteau |
| 9,402,844 | B2 | 8/2016 | Tabuteau |
| 9,408,815 | B2 | 8/2016 | Tabuteau |
| 9,421,176 | B1 | 8/2016 | Tabuteau |
| 9,457,023 | B1 | 10/2016 | Tabuteau |
| 9,457,025 | B2 | 10/2016 | Tabuteau |
| 9,474,731 | B1 | 10/2016 | Tabuteau |
| 9,486,450 | B2 | 11/2016 | Tabuteau |
| 9,700,528 | B2 | 7/2017 | Tabuteau |
| 9,700,553 | B2 | 7/2017 | Tabuteau |
| 9,707,191 | B2 | 7/2017 | Tabuteau |
| 9,763,932 | B2 | 9/2017 | Tabuteau |
| 9,861,595 | B2 | 1/2018 | Tabuteau |
| 9,867,819 | B2 | 1/2018 | Tabuteau |
| 9,968,568 | B2 | 5/2018 | Tabuteau |
| 10,058,518 | B2 | 8/2018 | Tabuteau |
| 10,064,857 | B2 | 9/2018 | Tabuteau |
| 10,080,727 | B2 | 9/2018 | Tabuteau |
| 10,092,560 | B2 | 10/2018 | Tabuteau |
| 10,092,561 | B2 | 10/2018 | Tabuteau |
| 10,105,327 | B2 | 10/2018 | Tabuteau |
| 10,105,361 | B2 | 10/2018 | Tabuteau |
| 10,251,879 | B2 | 4/2019 | Tabuteau |
| 10,463,634 | B2 | 11/2019 | Tabuteau |

(Continued)

FOREIGN PATENT DOCUMENTS

| | | | |
|---|---|---|---|
| BR | 102016010170 | A2 | 11/2017 |
| EP | 4183391 | A1 | 5/2023 |

(Continued)

OTHER PUBLICATIONS

Spravato (esketamine), Highlights of Prescribing Information, revised Jul. 2020.
Nuedexta (dextromethorphan hydrobromide and quinidine sulfate), Highlights of Prescribing Information, revised Dec. 2022.
Aplenzin (bupropion hydrobromide), Highlights of Prescribing Information, revised Mar. 2022.
Tod et al., Quantitative Prediction of Cytochrome P450 (CYP) 2D6-Mediated Drug Interactions, Clinical Pharmacokinetics, 50(8), 519-530, Aug. 2011.
Kotlyar et al., Inhibition of CYP2D6 Activity by Bupropion, Journal of Clinical Psychopharmacology, 25(2), 226-229, Jun. 2005.
Pope et al., Pharmacokinetics of Dextromethorphan after Single or Multiple Dosing in Combination with Quinidine in Extensive and Poor Metabolizers, The Journal of Clinical Pharmacology, 44(10), 1132-1142, Oct. 2004.

(Continued)

*Primary Examiner* — Susan T Tran
(74) *Attorney, Agent, or Firm* — PROCOPIO, CORY, HARGREAVES & SAVITCH LLP; Brent Johnson; Yuefen Zhou

(57) ABSTRACT

This disclosure relates to administration of a combination of: 1) about 100-110 mg, about 104-106 mg, or about 105 mg or less of bupropion hydrochloride, or a molar equivalent amount of the free base form or another salt form of bupropion; and 2) about 40-50 mg, about 44-46 mg, or about 45 mg or less of dextromethorphan hydrobromide, or a molar equivalent amount of the free base form or another salt form of dextromethorphan in human patients for treating neurological and psychiatric conditions, such as agitation associated Alzheimer's disease and/or reducing relapse of agitation in Alzheimer's disease.

29 Claims, 5 Drawing Sheets

(56) References Cited

U.S. PATENT DOCUMENTS

| | | | |
|---|---|---|---|
| 10,512,643 | B2 | 12/2019 | Tabuteau |
| 10,548,857 | B2 | 2/2020 | Tabuteau |
| 10,596,167 | B2 | 3/2020 | Tabuteau |
| 10,688,066 | B2 | 6/2020 | Tabuteau |
| 10,695,304 | B2 | 6/2020 | Tabuteau |
| 10,772,850 | B2 | 9/2020 | Tabuteau |
| 10,780,064 | B2 | 9/2020 | Tabuteau |
| 10,780,066 | B2 | 9/2020 | Tabuteau |
| 10,786,469 | B2 | 9/2020 | Tabuteau |
| 10,786,496 | B2 | 9/2020 | Tabuteau |
| 10,799,497 | B2 | 10/2020 | Tabuteau |
| 10,806,710 | B2 | 10/2020 | Tabuteau |
| 10,813,924 | B2 | 10/2020 | Tabuteau |
| 10,864,209 | B2 | 12/2020 | Tabuteau |
| 10,874,663 | B2 | 12/2020 | Tabuteau |
| 10,874,664 | B2 | 12/2020 | Tabuteau |
| 10,874,665 | B2 | 12/2020 | Tabuteau |
| 10,881,624 | B2 | 1/2021 | Tabuteau |
| 10,881,657 | B2 | 1/2021 | Tabuteau |
| 10,894,046 | B2 | 1/2021 | Tabuteau |
| 10,894,047 | B2 | 1/2021 | Tabuteau |
| 10,898,453 | B2 | 1/2021 | Tabuteau |
| 10,925,842 | B2 | 2/2021 | Tabuteau |
| 10,933,034 | B2 | 3/2021 | Tabuteau |
| 10,940,124 | B2 | 3/2021 | Tabuteau |
| 10,945,973 | B2 | 3/2021 | Tabuteau |
| 10,966,941 | B2 | 4/2021 | Tabuteau |
| 10,966,942 | B2 | 4/2021 | Tabuteau |
| 10,966,974 | B2 | 4/2021 | Tabuteau |
| 10,980,800 | B2 | 4/2021 | Tabuteau |
| 11,007,189 | B2 | 5/2021 | Tabuteau |
| 11,020,389 | B2 | 6/2021 | Tabuteau |
| 11,058,648 | B2 | 7/2021 | Tabuteau |
| 11,065,248 | B2 | 7/2021 | Tabuteau |
| 11,090,300 | B2 | 8/2021 | Tabuteau |
| 11,096,937 | B2 | 8/2021 | Tabuteau |
| 11,123,343 | B2 | 9/2021 | Tabuteau |
| 11,123,344 | B2 | 9/2021 | Tabuteau |
| 11,129,826 | B2 | 9/2021 | Tabuteau |
| 11,141,388 | B2 | 10/2021 | Tabuteau |
| 11,141,416 | B2 | 10/2021 | Tabuteau |
| 11,147,808 | B2 | 10/2021 | Tabuteau |
| 11,185,515 | B2 | 11/2021 | Tabuteau |
| 11,191,739 | B2 | 12/2021 | Tabuteau |
| 11,197,839 | B2 | 12/2021 | Tabuteau |
| 11,207,281 | B2 | 12/2021 | Tabuteau |
| 11,213,521 | B2 | 1/2022 | Tabuteau |
| 11,229,640 | B2 | 1/2022 | Tabuteau |
| 11,234,946 | B2 | 2/2022 | Tabuteau |
| 11,253,491 | B2 | 2/2022 | Tabuteau |
| 11,253,492 | B2 | 2/2022 | Tabuteau |
| 11,273,133 | B2 | 3/2022 | Tabuteau |
| 11,273,134 | B2 | 3/2022 | Tabuteau |
| 11,285,118 | B2 | 3/2022 | Tabuteau |
| 11,285,146 | B2 | 3/2022 | Tabuteau |
| 11,291,638 | B2 | 4/2022 | Tabuteau |
| 11,291,665 | B2 | 4/2022 | Tabuteau |
| 11,298,351 | B2 | 4/2022 | Tabuteau |
| 11,298,352 | B2 | 4/2022 | Tabuteau |
| 11,311,534 | B2 | 4/2022 | Tabuteau |
| 11,344,544 | B2 | 5/2022 | Tabuteau |
| 11,357,744 | B2 | 6/2022 | Tabuteau |
| 11,364,233 | B2 | 6/2022 | Tabuteau |
| 11,382,874 | B2 | 7/2022 | Tabuteau |
| 11,419,867 | B2 | 8/2022 | Tabuteau |
| 11,426,370 | B2 | 8/2022 | Tabuteau |
| 11,426,401 | B2 | 8/2022 | Tabuteau |
| 11,433,067 | B2 | 9/2022 | Tabuteau |
| 11,439,636 | B1 | 9/2022 | Tabuteau |
| 11,478,468 | B2 | 10/2022 | Tabuteau |
| 11,497,721 | B2 | 11/2022 | Tabuteau |
| 11,510,918 | B2 | 11/2022 | Tabuteau |
| 11,517,542 | B2 | 12/2022 | Tabuteau |
| 11,517,543 | B2 | 12/2022 | Tabuteau |
| 11,517,544 | B2 | 12/2022 | Tabuteau |
| 11,524,007 | B2 | 12/2022 | Tabuteau |
| 11,524,008 | B2 | 12/2022 | Tabuteau |
| 11,534,414 | B2 | 12/2022 | Tabuteau |
| 11,541,021 | B2 | 1/2023 | Tabuteau |
| 11,541,048 | B2 | 1/2023 | Tabuteau |
| 11,571,399 | B2 | 2/2023 | Tabuteau |
| 11,571,417 | B2 | 2/2023 | Tabuteau |
| 11,576,877 | B2 | 2/2023 | Tabuteau |
| 11,576,909 | B2 | 2/2023 | Tabuteau |
| 11,590,124 | B2 | 2/2023 | Tabuteau |
| 11,596,627 | B2 | 3/2023 | Tabuteau |
| 11,617,728 | B2 | 4/2023 | Tabuteau |
| 11,617,747 | B2 | 4/2023 | Tabuteau |
| 11,628,149 | B2 | 4/2023 | Tabuteau |
| 11,660,273 | B2 | 5/2023 | Tabuteau |
| 11,660,274 | B2 | 5/2023 | Tabuteau |
| 11,717,518 | B1 | 8/2023 | Tabuteau |
| 11,730,706 | B1 | 8/2023 | Tabuteau |
| 11,752,144 | B1 | 9/2023 | Tabuteau |
| 11,779,579 | B2 | 10/2023 | Tabuteau |
| 11,839,612 | B1 | 12/2023 | Tabuteau |
| 11,844,797 | B1 | 12/2023 | Tabuteau |
| 11,883,373 | B1 | 1/2024 | Tabuteau |
| 11,896,563 | B2 | 2/2024 | Tabuteau |
| 11,925,636 | B2 | 3/2024 | Tabuteau |
| 11,969,421 | B2 | 4/2024 | Tabuteau |
| 11,986,444 | B2 | 5/2024 | Tabuteau |
| 12,036,191 | B1 | 7/2024 | Tabuteau |
| 12,042,473 | B2 | 7/2024 | Tabuteau |
| 12,109,178 | B2 | 10/2024 | Tabuteau |
| 12,138,260 | B2 | 11/2024 | Tabuteau |
| 12,146,889 | B1 | 11/2024 | Tabuteau |
| 12,156,914 | B2 | 12/2024 | Tabuteau |
| 12,194,005 | B2 | 1/2025 | Tabuteau |
| 12,194,006 | B2 | 1/2025 | Tabuteau |
| 12,194,036 | B2 | 1/2025 | Tabuteau |
| 12,239,642 | B2 | 3/2025 | Tabuteau |
| 12,263,161 | B2 | 4/2025 | Tabuteau |
| 12,310,961 | B2 | 5/2025 | Tabuteau |
| 12,364,674 | B2 | 7/2025 | Tabuteau |
| 12,370,154 | B2 | 7/2025 | Tabuteau |
| 12,377,091 | B2 | 8/2025 | Tabuteau |
| 12,390,428 | B2 | 8/2025 | Tabuteau |
| 12,433,884 | B2 | 10/2025 | Tabuteau |
| 12,447,138 | B2 | 10/2025 | Tabuteau |
| 12,472,155 | B2 | 11/2025 | Tabuteau |
| 12,472,156 | B2 | 11/2025 | Tabuteau |
| 12,472,174 | B2 | 11/2025 | Tabuteau |
| 12,478,622 | B2 | 11/2025 | Tabuteau |
| 2002/0035105 | A1 | 3/2002 | Caruso |
| 2003/0044462 | A1 | 3/2003 | Subramanian et al. |
| 2008/0044462 | A1 | 2/2008 | Trumbore et al. |
| 2010/0040679 | A1 | 2/2010 | Chang |
| 2010/0291225 | A1 | 11/2010 | Fanda et al. |
| 2015/0126541 | A1 | 5/2015 | Tabuteau |
| 2015/0126542 | A1 | 5/2015 | Tabuteau |
| 2015/0126543 | A1 | 5/2015 | Tabuteau |
| 2015/0126544 | A1 | 5/2015 | Tabuteau |
| 2015/0133485 | A1 | 5/2015 | Tabuteau |
| 2015/0133486 | A1 | 5/2015 | Tabuteau |
| 2015/0150830 | A1 | 6/2015 | Tabuteau |
| 2015/0157582 | A1 | 6/2015 | Tabuteau |
| 2015/0342947 | A1 | 12/2015 | Pollard et al. |
| 2016/0008352 | A1 | 1/2016 | Tabuteau |
| 2016/0030420 | A1 | 2/2016 | Tabuteau |
| 2016/0030421 | A1 | 2/2016 | Tabuteau |
| 2016/0128944 | A1 | 5/2016 | Chawrai et al. |
| 2016/0128998 | A1 | 5/2016 | Tabuteau |
| 2016/0136155 | A1 | 5/2016 | Tabuteau |
| 2016/0199321 | A1 | 7/2016 | Tabuteau |
| 2016/0228390 | A1 | 8/2016 | Tabuteau |
| 2016/0263099 | A1 | 9/2016 | Tabuteau |
| 2016/0263100 | A1 | 9/2016 | Tabuteau |
| 2016/0317475 | A1 | 11/2016 | Tabuteau |
| 2016/0317476 | A1 | 11/2016 | Tabuteau |
| 2016/0324807 | A1 | 11/2016 | Tabuteau |
| 2016/0339017 | A1 | 11/2016 | Tabuteau |
| 2016/0346276 | A1 | 12/2016 | Tabuteau |
| 2016/0361305 | A1 | 12/2016 | Tabuteau |

(56) References Cited

U.S. PATENT DOCUMENTS

2016/0375008 A1 12/2016 Tabuteau
2016/0375012 A1 12/2016 Tabuteau
2017/0007558 A1 1/2017 Tabuteau
2017/0014357 A1 1/2017 Tabuteau
2017/0252309 A1 9/2017 Tabuteau
2017/0281617 A1 10/2017 Tabuteau
2017/0304229 A1 10/2017 Tabuteau
2017/0304230 A1 10/2017 Tabuteau
2017/0304298 A1 10/2017 Tabuteau
2017/0354619 A1 12/2017 Tabuteau
2017/0360773 A1 12/2017 Tabuteau
2017/0360774 A1 12/2017 Tabuteau
2017/0360776 A1 12/2017 Tabuteau
2018/0092906 A1 4/2018 Tabuteau
2018/0116980 A1 5/2018 Tabuteau
2018/0133195 A1 5/2018 Tabuteau
2018/0207151 A1 7/2018 Tabuteau
2018/0256518 A1 9/2018 Tabuteau
2018/0360823 A1 12/2018 Tabuteau
2019/0000835 A1 1/2019 Tabuteau
2019/0008800 A1 1/2019 Tabuteau
2019/0008801 A1 1/2019 Tabuteau
2019/0008805 A1 1/2019 Tabuteau
2019/0015407 A1 1/2019 Tabuteau
2019/0083426 A1 3/2019 Tabuteau
2019/0142768 A1 5/2019 Tabuteau
2019/0192450 A1 6/2019 Tabuteau
2019/0192507 A1 6/2019 Tabuteau
2019/0216798 A1 7/2019 Tabuteau
2019/0216800 A1 7/2019 Tabuteau
2019/0216801 A1 7/2019 Tabuteau
2019/0290601 A1 9/2019 Tabuteau
2020/0022929 A1 1/2020 Tabuteau
2020/0093762 A1 3/2020 Tabuteau
2020/0147008 A1 5/2020 Tabuteau
2020/0147075 A1* 5/2020 Tabuteau ............. A61K 31/137
2020/0206217 A1 7/2020 Tabuteau
2020/0215055 A1 7/2020 Tabuteau
2020/0215056 A1 7/2020 Tabuteau
2020/0215057 A1 7/2020 Tabuteau
2020/0215058 A1 7/2020 Tabuteau
2020/0215059 A1 7/2020 Tabuteau
2020/0222389 A1 7/2020 Tabuteau
2020/0230078 A1 7/2020 Tabuteau
2020/0230129 A1 7/2020 Tabuteau
2020/0230130 A1 7/2020 Tabuteau
2020/0230131 A1 7/2020 Tabuteau
2020/0237751 A1 7/2020 Tabuteau
2020/0237752 A1 7/2020 Tabuteau
2020/0246280 A1 8/2020 Tabuteau
2020/0261431 A1 8/2020 Tabuteau
2020/0297666 A1 9/2020 Tabuteau
2020/0338022 A1 10/2020 Tabuteau
2020/0360310 A1 11/2020 Tabuteau
2020/0397723 A1 12/2020 Tabuteau
2020/0397724 A1 12/2020 Tabuteau
2020/0405664 A1 12/2020 Tabuteau
2021/0000763 A1 1/2021 Tabuteau
2021/0000764 A1 1/2021 Tabuteau
2021/0000765 A1 1/2021 Tabuteau
2021/0000768 A1 1/2021 Tabuteau
2021/0000820 A1 1/2021 Tabuteau
2021/0015768 A1 1/2021 Tabuteau
2021/0015814 A1 1/2021 Tabuteau
2021/0015815 A1 1/2021 Tabuteau
2021/0023075 A1 1/2021 Tabuteau
2021/0023076 A1 1/2021 Tabuteau
2021/0030747 A1 2/2021 Tabuteau
2021/0030749 A1 2/2021 Tabuteau
2021/0030750 A1 2/2021 Tabuteau
2021/0030751 A1 2/2021 Tabuteau
2021/0046067 A1 2/2021 Tabuteau
2021/0052521 A1 2/2021 Tabuteau
2021/0060004 A1 3/2021 Tabuteau
2021/0060005 A1 3/2021 Tabuteau
2021/0069125 A1 3/2021 Tabuteau
2021/0069128 A1 3/2021 Tabuteau
2021/0077428 A1 3/2021 Tabuteau
2021/0077429 A1 3/2021 Tabuteau
2021/0077483 A1 3/2021 Tabuteau
2021/0106546 A1 4/2021 Tabuteau
2021/0177834 A1 6/2021 Tabuteau
2021/0186899 A1 6/2021 Tabuteau
2021/0186900 A1 6/2021 Tabuteau
2021/0186901 A1 6/2021 Tabuteau
2021/0186955 A1 6/2021 Tabuteau
2021/0186956 A1 6/2021 Tabuteau
2021/0196704 A1 7/2021 Tabuteau
2021/0196705 A1 7/2021 Tabuteau
2021/0205239 A1 7/2021 Tabuteau
2021/0205240 A1 7/2021 Tabuteau
2021/0205297 A1 7/2021 Tabuteau
2021/0220293 A1 7/2021 Tabuteau
2021/0220294 A1 7/2021 Tabuteau
2021/0220348 A1 7/2021 Tabuteau
2021/0260054 A1 8/2021 Tabuteau
2021/0267967 A1 9/2021 Tabuteau
2021/0338605 A1 11/2021 Tabuteau
2021/0346370 A1 11/2021 Tabuteau
2021/0361645 A1 11/2021 Tabuteau
2021/0401828 A1 12/2021 Tabuteau
2021/0401829 A1 12/2021 Tabuteau
2021/0401830 A1 12/2021 Tabuteau
2021/0401831 A1 12/2021 Tabuteau
2022/0008363 A1 1/2022 Tabuteau
2022/0071930 A1 3/2022 Tabuteau
2022/0071931 A1 3/2022 Tabuteau
2022/0079892 A1 3/2022 Tabuteau
2022/0096462 A1 3/2022 Tabuteau
2022/0105086 A1 4/2022 Tabuteau
2022/0133655 A1 5/2022 Tabuteau
2022/0142950 A1 5/2022 Tabuteau
2022/0193012 A1 6/2022 Tabuteau
2022/0218631 A1 7/2022 Tabuteau
2022/0218698 A1 7/2022 Tabuteau
2022/0233470 A1 7/2022 Tabuteau
2022/0233474 A1 7/2022 Tabuteau
2022/0233518 A1 7/2022 Tabuteau
2022/0233519 A1 7/2022 Tabuteau
2022/0241220 A1 8/2022 Tabuteau
2022/0241221 A1 8/2022 Tabuteau
2022/0241269 A1 8/2022 Tabuteau
2022/0241270 A1 8/2022 Tabuteau
2022/0265639 A1 8/2022 Tabuteau
2022/0280504 A1 9/2022 Tabuteau
2022/0313689 A1 10/2022 Tabuteau
2022/0323381 A1 10/2022 Tabuteau
2022/0378779 A1 12/2022 Tabuteau
2023/0045675 A1 2/2023 Tabuteau
2023/0096437 A1 3/2023 Tabuteau
2023/0099206 A1 3/2023 Tabuteau
2023/0100008 A1 3/2023 Tabuteau
2023/0100913 A1 3/2023 Tabuteau
2023/0114111 A1 4/2023 Tabuteau
2023/0131854 A1 4/2023 Tabuteau
2023/0142244 A1 5/2023 Tabuteau
2023/0210843 A1 7/2023 Tabuteau
2023/0218550 A1 7/2023 Tabuteau
2023/0225995 A1 7/2023 Tabuteau
2023/0233491 A1 7/2023 Tabuteau
2023/0241010 A1 8/2023 Tabuteau
2023/0248668 A1 8/2023 Tabuteau
2023/0248669 A1 8/2023 Tabuteau
2023/0255905 A1 8/2023 Tabuteau
2023/0263750 A1 8/2023 Tabuteau
2023/0270740 A1 8/2023 Tabuteau
2023/0277478 A1 9/2023 Tabuteau
2023/0277479 A1 9/2023 Tabuteau
2023/0277480 A1 9/2023 Tabuteau
2023/0277481 A1 9/2023 Tabuteau
2023/0277504 A1 9/2023 Tabuteau
2023/0293456 A1 9/2023 Tabuteau
2024/0000770 A1 1/2024 Tabuteau
2024/0016797 A1 1/2024 Tabuteau

(56) References Cited

U.S. PATENT DOCUMENTS

| | | | | |
|---|---|---|---|---|
| 2024/0024309 | A1 | 1/2024 | Tabuteau | |
| 2024/0041862 | A1 | 2/2024 | Tabuteau | |
| 2024/0041863 | A1 | 2/2024 | Tabuteau | |
| 2024/0050383 | A1 | 2/2024 | Tabuteau | |
| 2024/0066025 | A1 | 2/2024 | Tabuteau | |
| 2024/0115524 | A1 | 4/2024 | Tabuteau | |
| 2024/0148719 | A1 | 5/2024 | Tabuteau | |
| 2024/0156751 | A1 * | 5/2024 | Tabuteau | A61K 31/485 |
| 2024/0165104 | A1 | 5/2024 | Tabuteau | |
| 2024/0189302 | A1 | 6/2024 | Tabuteau | |
| 2024/0197656 | A1 | 6/2024 | Tabuteau | |
| 2024/0197720 | A1 | 6/2024 | Tabuteau | |
| 2024/0238276 | A1 | 7/2024 | Tabuteau | |
| 2024/0252451 | A1 | 8/2024 | Tabuteau | |
| 2024/0269130 | A1 | 8/2024 | Tabuteau | |
| 2024/0299319 | A1 | 9/2024 | Tabuteau | |
| 2024/0299320 | A1 | 9/2024 | Tabuteau | |
| 2024/0307408 | A1 | 9/2024 | Tabuteau | |
| 2024/0390297 | A1 | 11/2024 | Tabuteau | |
| 2024/0408040 | A1 | 12/2024 | Tabuteau | |
| 2025/0009754 | A1 | 1/2025 | Tabuteau | |
| 2025/0012821 | A1 | 1/2025 | Tabuteau | |
| 2025/0025458 | A1 | 1/2025 | Tabuteau | |
| 2025/0032432 | A1 | 1/2025 | Tabuteau | |
| 2025/0064797 | A1 | 2/2025 | Tabuteau | |
| 2025/0073188 | A1 | 3/2025 | Tabuteau | |
| 2025/0090521 | A1 | 3/2025 | Tabuteau | |
| 2025/0177380 | A1 | 6/2025 | Tabuteau | |
| 2025/0186428 | A1 | 6/2025 | Tabuteau | |
| 2025/0241907 | A1 | 7/2025 | Tabuteau | |
| 2025/0262175 | A1 | 8/2025 | Tabuteau | |
| 2025/0268890 | A1 | 8/2025 | Tabuteau | |
| 2025/0268891 | A1 | 8/2025 | Tabuteau | |
| 2025/0281430 | A1 | 9/2025 | Tabuteau | |
| 2025/0319043 | A1 | 10/2025 | Tabuteau | |
| 2025/0325539 | A1 | 10/2025 | Tabuteau | |
| 2025/0332123 | A1 | 10/2025 | Tabuteau | |
| 2025/0345294 | A1 | 11/2025 | Tabuteau | |
| 2025/0367142 | A1 | 12/2025 | Tabuteau | |

FOREIGN PATENT DOCUMENTS

| | | | | |
|---|---|---|---|---|
| KR | 101612197 | B1 | 4/2016 | |
| WO | 1998050044 | | 11/1998 | |
| WO | 2003086362 | A2 | 10/2003 | |
| WO | 2004089873 | A1 | 10/2004 | |
| WO | 2009006194 | | 1/2009 | |
| WO | 2009050726 | A2 | 4/2009 | |
| WO | 2015069809 | A1 | 5/2015 | |
| WO | 2016125108 | A1 | 8/2016 | |
| WO | 2019165379 | A1 | 8/2019 | |
| WO | 2020146412 | A1 | 7/2020 | |
| WO | 2021202329 | A1 | 10/2021 | |
| WO | 2021202419 | A1 | 10/2021 | |
| WO | 2022119981 | A1 | 6/2022 | |
| WO | 2023004064 | A1 | 1/2023 | |
| WO | 2023019138 | A1 | 2/2023 | |
| WO | 2023225511 | A1 | 11/2023 | |
| WO | 2024011138 | A1 | 1/2024 | |
| WO | WO-2024118570 | A1 * | 6/2024 | A61K 9/209 |

OTHER PUBLICATIONS

Auvelity (dextromethorphan hydrobromide and bupropion hydrochloride), Highlights of Prescribing Information and Medication Guide, issued Dec. 2022.

International Preliminary Report on Patentability, PCT/US2021/061492, mailed on Jun. 15, 2023.

International Search Report and Written Opinion, PCT/US2021/061492 received on Jun. 15, 2023.

International Search Report and Written Opinion, PCT/US2022/012768 received on Jul. 5, 2023.

International Search Report and Written Opinion, PCT/US2023/067062 mailed on Jul. 12, 2023.

Axsome Therapeutics Announces Topline Results of the Stride-1 Phase 3 Trial in Treatment Resistant Depression and Expert Call to Discuss Clinical Implications, Mar. 2020 (retrieved from internet on Jul. 19, 2023). <axsometherapeuticsinc.gcs-web.com/node/9176/pdf>.

Anderson, A.; et al. "Efficacy and Safety of AXS-05, an Oral NMDA Receptor Antagonist with Multimodal Activity, in Major Depressive Disorder: Results of a Phase 2, Double-Blind, Active-Controlled Trial" ASCP Annual Meeting 2019 (retrieved from internet on Jul. 19, 2023). <d3dyybxyjb4kyh.cloudfront.net/pdfs/SOBP+2021+AXS-05+MDD+Poster+FINAL.pdf> (May 2019).

O'Gorman, C; et al. "Rapid Effects of AXS 05, an Oral NMDA Receptor Antagonist, in Major Depressive Disorder: Results from Two Randomized, Double Blind, Controlled Trials" ASCP Annual Meeting 2021 (retrieved from internet on Jul. 19, 2023). <d3dyybxyjb4kyh.cloudfront.net/pdfs/SOBP+2021+AXS-05+MDD+Poster+FINAL.pdf> (Jun. 2021).

O'Gorman, C.; et al. "PMH40 Effects of AXS-05 on Patient Reported Depressive Symptoms in Major Depressive Disorder: Results from the GEMINI Trial" <doi.org/10.1016/j.jval.2021.04.662> (retrieved from internet on Jul. 19, 2023). Value in Health, Jun. 2021, vol. 24, Supplement 1, pp. S135.

O'Gorman, C.; et al. "P246. Rapid Antidepressant Effects and MADRS Core Symptom Improvements With AXS-05, an Oral NMDA Receptor Antagonist, in Major Depressive Disorder: Results From Two Randomized, Double-Blind, Controlled Trials" ACNP 60th Annual Meeting: Poster Abstracts P246 <nature.com/articles/s41386-021-01236-7> (retrieved from internet on Jul. 19, 2023). Neuropsychopharmacol. 46 (Suppl 1), 72-217, Dec. 2021.

International Preliminary Report on Patentability, PCT/US2022/012768, mailed on Jul. 27, 2023.

Nofziger et al., Evaluation of dextromethorphan with select anti-depressant therapy for the treatment of depression in the acute care psychiatric setting, Mental Health Clinician, 9(2), 76-81, Mar. 2019.

Update: Bupropion Hydrochloride Extended-Release 300 mg Bioequivalence Studies, FDA, retrieved Mar. 2021.

FDA Draft Guidance on Bupropion Hydrochloride, revised Mar. 2013.

Forfivo XL (bupropion hydrochloride) extended-release tablets, for oral use, Highlights of Prescribing Information, revised Dec. 2019.

Forfivo XL (Bupropion HCI) extended-release tablet, NDA 22497, Jan. 25, 2010.

Wellbutrin XL (bupropion hydrochloride extended-release), Highlights of Prescribing Information, revised Mar. 2022.

Baker T. E. et al., Human Milk and Plasma Pharmacokinetics of Single-Dose Rimegepant 75mg in Healthy Lactating Women, Breastfeeding Medicine, 17(3), 277-282, 2022.

Berle J. O. et al., Antidepressant Use During Breastfeeding, Current Women's Health Reviews, 7(1), 28-34, Feb. 2011.

Briggs G. G. et al., Excretion of bupropion in breast milk, Annals of Pharmacotherapy, 27(4):431-433, Apr. 1993.

Chad L. et al., Update on antidepressant use during breastfeeding, Canadian Family Physician, 59(6), 633-634, Jun. 2013.

Chaudron L. H. et al., Bupropion and Breastfeeding: A case of a possible Infant Seizure, The Journal of clinical psychiatry, 65(6), 881-882, Jun. 2004.

Davis M. F. et al., Bupropion Levels in Breast Milk for 4 Mother-Infant Pairs: More Answers to Lingering Questions, J. Clin. Psychiatry, 70(2), 297-298, Feb. 2009.

Di Scalea T. L. et al., Antidepressant Medication Use during Breastfeeding, Clinical obstetrics and gynecology, 52 (3): 483-497, Sep. 2009.

Dwoskin L. P. et al., Review of the Pharmacology and Clinical Profile of Bupropion, and Antidepressant and Tobacco Use Cessation Agent, CNS Drug Reviews, 12(3-4), 178-207, Sep. 2006.

Gentile S, The safety of newer antidepressants in pregnancy and breastfeeding, Drug Safety, 28(2), 137-152, Feb. 2005. [doi: 10.2165/00002018-200528020-00005. PMID: 15691224.].

Haas J. S. et al., Bupropion in breast milk: an exposure assessment for potential treatment to prevent post-partum tobacco use, Tobacco Control, 13(1), 52-56, Mar. 2004.

(56) References Cited

OTHER PUBLICATIONS

Ram D. et al., Antidepressants, anxiolytics, and hypnotics in pregnancy and lactation, Indian J Psychiatry, 57(Suppl 2): S354-S371, Jul. 2015. [doi: 10.4103/0019-5545.161504].
Weissman A. M. et al., Pooled Analysis of Antidepressant Levels in Lactating Mothers, Breast Milk, and Nursing Infants, Am J Psychiatry, 161(6), 1066-1078, Jun. 2004.
Horn J. R. et al., Get to Know an Enzyme: CYP2D6, Pharmacy Times, Jul. 2008, retrieved on Aug. 28, 2023.
International Search Report and Written Opinion, PCT/US2023/069286 mailed on Aug. 22, 2023.
International Search Report and Written Opinion, PCT/US2023/069239 mailed on Aug. 28, 2023.
International Search Report and Written Opinion, PCT/US2023/069367 mailed on Aug. 28, 2023.
International Search Report and Written Opinion, PCT/US2023/069655 mailed on Sep. 15, 2023.
International Search Report and Written Opinion, PCT/US2023/069371 mailed on Sep. 26, 2023.
International Search Report and Written Opinion, PCT/US2022/037913 mailed on Sep. 21, 2022.
Jones A et al., "Early Improvements in Functioning and Quality of Life With AXS-05 in Major Depressive Disorder: Results From the Gemini Trial ," Value in Health, Jun. 2021, vol. 24, abstract No. PHM42, p. S135. DOI: 10.1016/j.jval.2021.04.662.
International Search Report and Written Opinion, PCT/US2022/074713 mailed on Sep. 21, 2022.
Axsome Therapeutics, Inc.: "Merit: A Randomized, Double-blind, Placebo-controlled Study of AXS-05 for Relapse Prevention in Treatment Resistant Depression," ClinicalTrials.gov, NCT04608396 version 2, Mar. 24, 2021.
International Preliminary Report on Patentability, PCT/US2022/037913, issued on Jan. 18, 2024.
International Preliminary Report on Patentability, PCT/US2022/074713, issued on Feb. 22, 2024.
Chinese Pat. No. 202080004041.1 Invalidation Notice and Request issued on Jan. 15, 2024. (English translation included).
Ward K. and Citrome L.: "AXS-05: an investigational treatment for Alzheimer's disease-associated agitation", Expert Opinion on Investigational Drugs, Jul. 6, 2022, vol. 31, issue 8, pp. 773-780, DOI: 10.1080/13543784.2022.2096006.
Defendant TEVA Pharmaceuticals, Inc.'s Invalidity Contentions for U.S. Pat. Nos. 11,752,144, 11,717,518, 11,730,706 and Exhibits A-C dated Apr. 11, 2024.
Goodnick, Psychotropic drugs and the ECG: focus on the QTc interval, Expert Opinion on Pharmacotherapy, vol. 3, No. 5, p. 479-498, 2002.
International Search Report and Written Opinion, PCT/US2024/046359 mailed on Nov. 28, 2024.
Tabuteau H, et al. "Effect of AXS-05 (Dextromethorphan-Bupropion) in Major Depressive Disorder: A Randomized Double-Blind Controlled Trial" Am J Psychiatry (2022) vol. 179 pp. 490-499. doi: 10.1176/appi.ajp.21080800.
International Preliminary Report on Patentability, PCT/US2023/067062, mailed on Nov. 28, 2024.
International Search Report and Written Opinion, PCT/US2024/043903 mailed on Nov. 28, 2024.
International Preliminary Report on Patentability, PCT/US2023/069286, mailed on Jan. 9, 2025.
International Preliminary Report on Patentability, PCT/US2023/069371, mailed on Jan. 9, 2025.
International Preliminary Report on Patentability, PCT/US2023/069655, mailed on Jan. 16, 2025.
Kotlyar et al., Effect of bupropion on physiological measures of stress in smokers during nicotine withdrawal, Pharmacology Biochemistry and Behavior, vol. 83, Issue 3, Mar. 2006, pp. 370-379. [https://doi.org/10.1016/j.pbb.2006.02.017].
International Search Report and Written Opinion, PCT/US2025/016339 mailed on Apr. 3, 2025.
Surovik, J.; et al. "A case of bupropion-induced Stevens-Johnson syndrome with acute psoriatic exacerbation," J. Drugs Dermatol. Aug. 2010, 9(8), 1010-1012. [Abstract].
Garcia, M.; et al. "Eosinophilia associated with bupropion," Int. J. Clin. Pharm. 2013, 35, 532-534. DOI: 10.1007/s11096-013-9803-y. [Abstract].
Ketenci, M.; et al. "Toxic Twist: A Case of Bupropion Induced Brugada Syndrome," Circulation 2023, 148, 1, Abstract 15984. DOI: 10.1161/circ.148.suppl_1.15984. [Abstract].
Ray, A.K.; et al. "Bupropion-Induced Acute Generalized Exanthematous Pustulosis," Pharmacotherapy 2012, 31(6), 621. DOI: 10.1592/phco.31.6.621. [Abstract].
Akbar, D.; et al. "Dextromethorphan-Bupropion for the Treatment of Depression: A Systematic Review of Efficacy and Safety in Clinical Trials," CNS Drugs 2023, 37(10), 867-881. DOI: 10.1007/s40263-023-01032-5. [Abstract].
Mccarthy B.; et al. "Dextromethorphan-bupropion (Auvelity) for the Treatment of Major Depressive Disorder," Clin. Psychopharmacol. Neurosci. 2023, 21(4), 609-616. DOI: 10.9758/cpn.23.1081.
Axsome Therapeutics, Inc. "A Trial of AXS-05 in Patients With Major Depressive Disorder (GEMINI)," Clinicaltrials.gov, NCT04019704 version 8, Sep. 16, 2022.
International Search Report and Written Opinion of the International Searching Authority for PCT/US25/30642, mailed on Jun. 18, 2025.
Iosifescu D. V. et al.: "Efficacy and Safety of AXS-05 (Dextromethorphan-Bupropion) in Patients With Major Depressive Disorder—A Phase 3 Randomized Clinical Trial (Gemini)", Journal of Clinical Psychiatry, 2022, vol. 83, No. 4, article 21ml4345, 9 pages. [DOI: 10.4088/JCP.21ml4345].
Axsome Therapeutics, Inc ..: "A Study to Assess the Efficacy and Safety of AXS-05 in Subjects With Treatment Resistant Major Depressive Disorder (STRIDE-I )", ClinicalTrials.gov, NCT02741791, update of Mar. 24, 2021.
Axsome Therapeutics, Inc.: "Open-Label Safety Study of AXS-05 in Subjects With TRD (Evolve)", ClinicalTrials.gov, NCT04634669, update of Mar. 7, 2023.
Bisset, Discontinuation of thioridazine, BMJ, vol. 325, p. 967-968, Oct. 26, 2002, bmj.com. [accessed on Jun. 11, 2025].
Jacobson et al., "AXS-05 in Treatment Resistant Depression (TRD) Stride-1 Phase 3 Trial Topline Results", Axsome Therapeutics, Mar. 30, 2020.
Montgomery et al., "A New Depression Scale Designed to be Sensitive to Change", British Journal of Psychiatry, vol. 134, No. 4, Apr. 1, 1979, pp. 382-389. (DOI: 10.1192/bjp.134.4.382).
Nobile et al., "Characteristics and treatment outcome of suicidal depression: Two large naturalistic cohorts of depressed outpatients", Australian and New Zealand Journal of Psychiatry, vol. 56, No. 4, pp. 347-364, 2022. (DOI: 10.1177/00048674211025697).
Jorge Lopez-Castroman et al., "Suicidal Depressed Patients Respond Less Well to Antidepressants in the Short Term", Depression and Anxiety, New York, NY, US, vol. 33, No. 6, Feb. 16, 2016, pp. 483-494. (DOI: 10.1002/DA.224 73).
Bartol et al., "Use-dependent drug-induced Brugada pattern caused by bupropion in an adolescent with depression", Journal of the American College of Cardiology, 77(18_Supplement_I), pp. 2117-2117, 2021.
International Search Report and Written Opinion, PCT/US2025/028224 mailed on Jul. 16, 2025.
Settle, "Tinnitus related to bupropion treatment", Psychiatry and Clinical Psychopharmacology 2014; 24: Supplement S339-S340.
Jerome, "Bupropion and drug-induced parkinsonism," The Canadian Journal of Psychiatry, 46(6), pp. 560-561, 2001.
International Search Report and Written Opinion, PCT/US2025/033094 mailed on Aug. 26, 2025.

* cited by examiner

FIG. 1 ACCORD randomized discontinuation study design

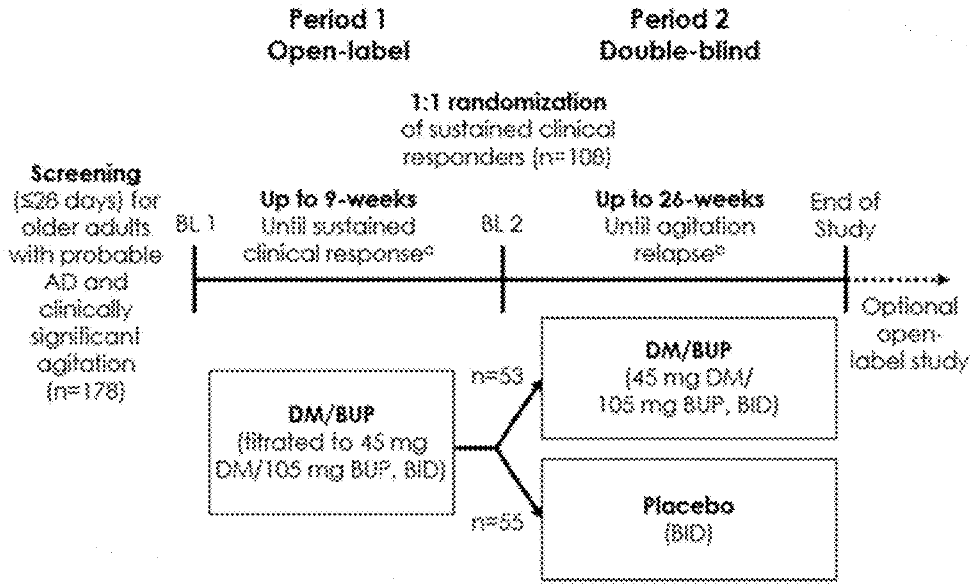

[a] Sustained response of ≥ 30% improvement from baseline in the CMAI total score and improvement on the PGI-C (score ≤3) that were both maintained for ≥4 consecutive weeks.

[b] Agitation relapse defined as a ≥10-point worsening in the CMAI total score from randomization or a CMAI total score greater than that at study entry; or hospitalization or other institutionalization due to ADA. AD, Alzheimer's disease; ADA, Alzheimer's disease-related agitation; BID, twice daily; BL, baseline; BUP, bupropion; CMAI, Cohen-Mansfield Agitation Inventory; DM, dextromethorphan; BUP, bupropion; PGI-C, Patient Global Impression of Change.

FIG. 2A Open-label period CMAI mean change from baseline
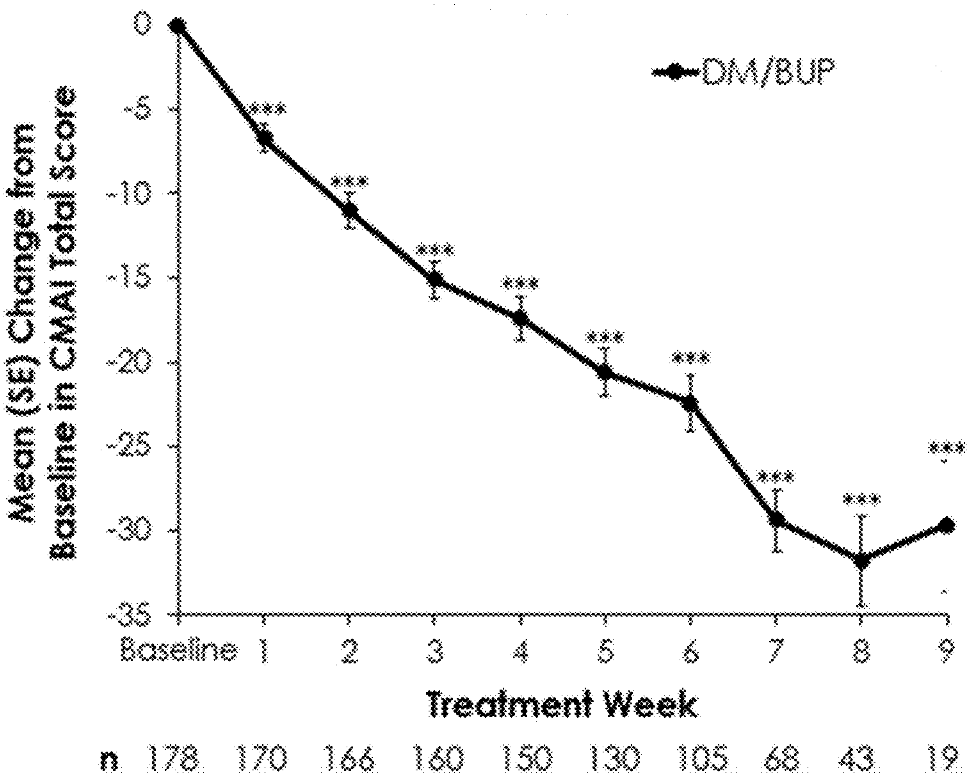
***P<0.001 for change from baseline, paired t-test at each time point.

FIG. 2B Open-label period participants with CMAI response
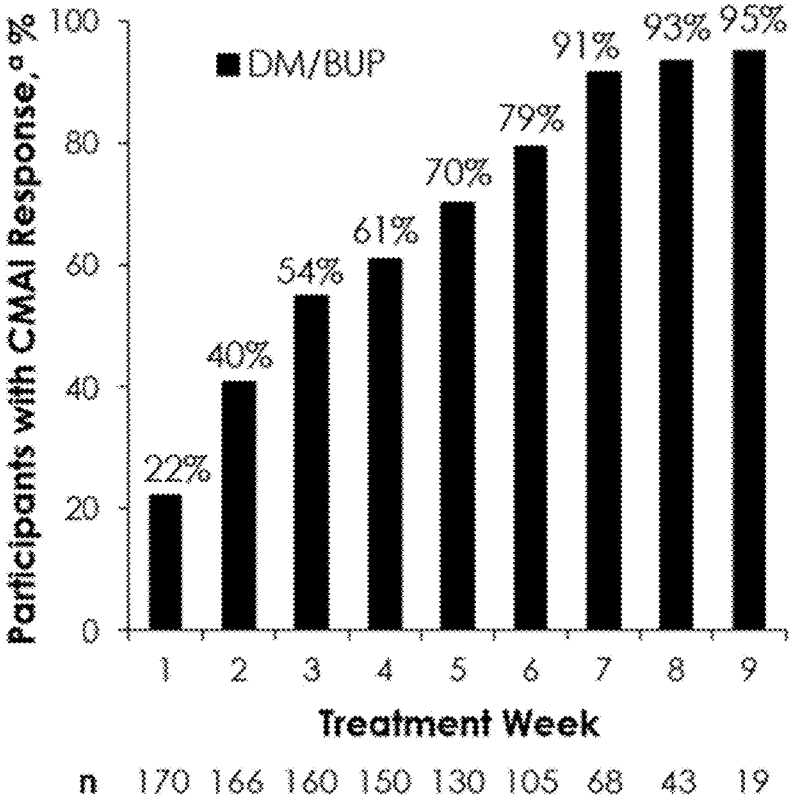
[a] CMAI response defined as ≥30% reduction from baseline. CMAI, Cohen-Mansfield Agitation Inventory.

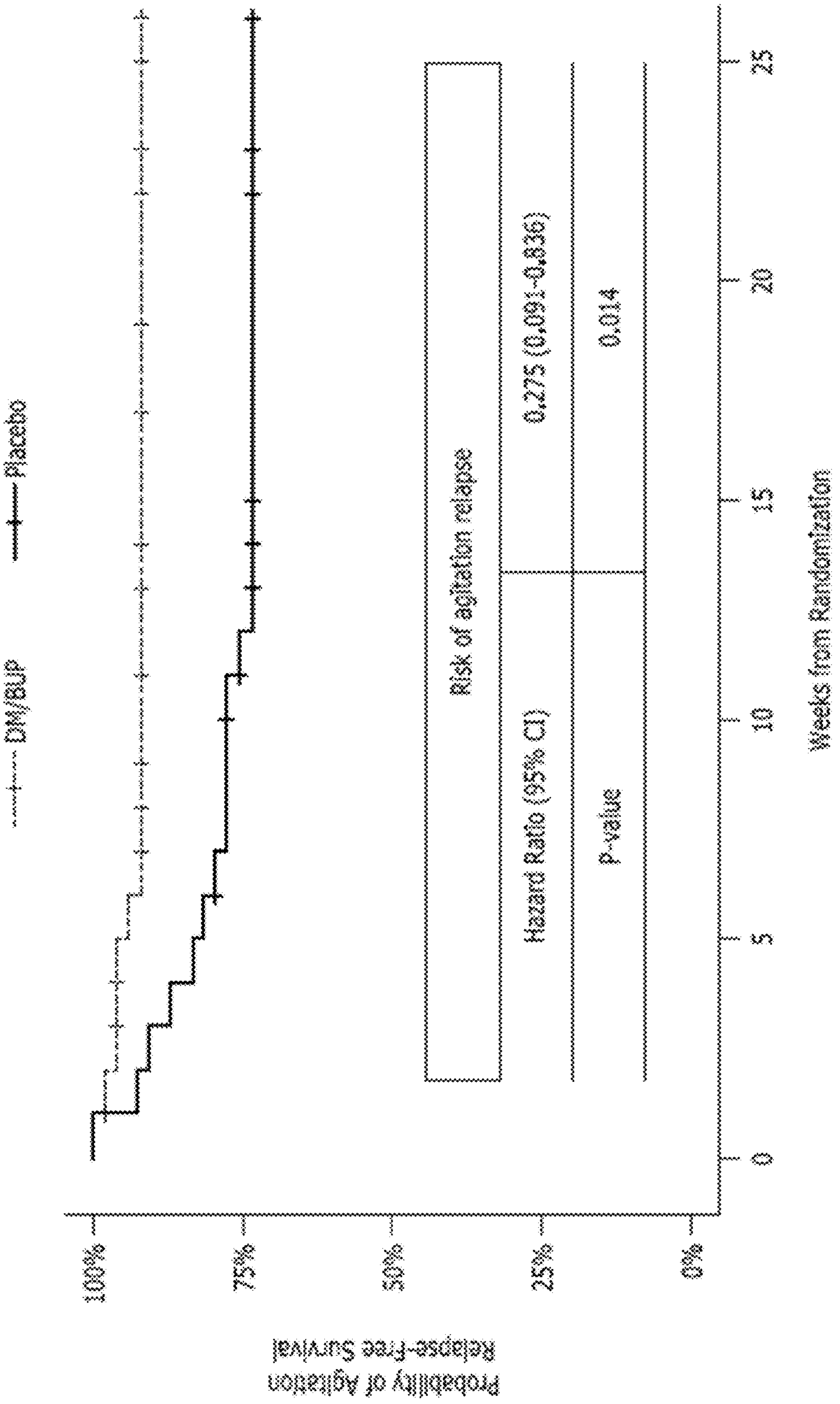
FIG. 3A Double-blind period probability of agitation relapse-free survival FIG. 3B Double-blind period probability of relapse incidence
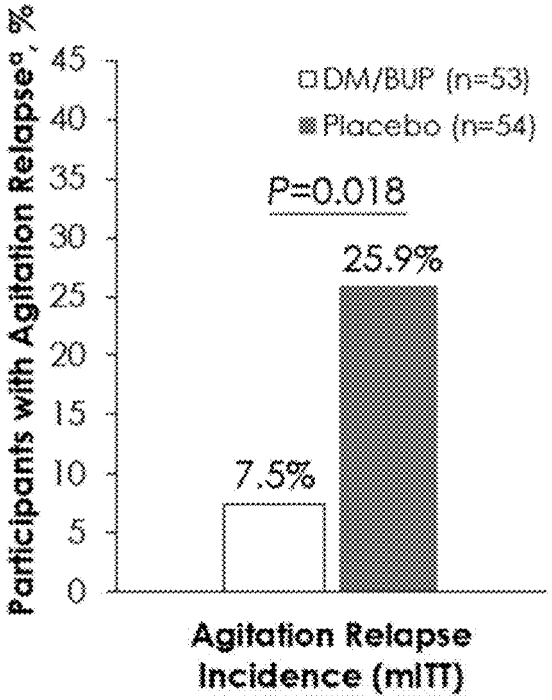
[a] Agitation relapse defined as a ≥10-point worsening (increase) in the CMAI total score from randomization or a CMAI total score greater than that at study entry for 2 consecutive weeks. CMAI, Cohen-Mansfield Agitation Inventory; mITT, modified intent-to-treat.

BUPROPION AS A MODULATOR OF DRUG ACTIVITY

CROSS REFERENCE TO RELATED APPLICATIONS

This application is a continuation of U.S. patent application Ser. No. 18/529,217, filed Dec. 5, 2023; which is a continuation of International Pat. App. No. PCT/US2023/081292, filed Nov. 28, 2023; which claims the benefit of U.S. Provisional App. Nos. 63/385,205, filed Nov. 28, 2022; 63/589,325, filed Oct. 11, 2023; and 63/589,525, filed Oct. 11, 2023; all of which are incorporated by reference herein in their entireties.

SUMMARY

This disclosure relates to administration of a combination of: 1) about 100-110 mg, about 104-106 mg, or about 105 mg of bupropion hydrochloride, or a molar equivalent amount of the free base form or another salt form of bupropion; and 2) about 40-50 mg, about 44-46 mg, or about 45 mg of dextromethorphan hydrobromide, or a molar equivalent amount of the free base form or another salt form of dextromethorphan (subject combination) to human beings.

Some embodiments include a method of treating agitation associated with Alzheimer's disease (AD) and/or delaying time to relapse of Alzheimer's disease agitation versus placebo to a human being, comprising: i) administering a combination of about 40-50 mg, about 44-46 mg, or about 45 mg of dextromethorphan hydrobromide, or a molar equivalent amount of the free base form or another salt form of dextromethorphan and about 100-110 mg, about 104-106 mg, or about 105 mg of bupropion hydrochloride, or a molar equivalent amount of the free base form or another salt form of bupropion to a human patient once daily or twice daily, wherein the human patient is experiencing Alzheimer's disease and/or agitation associated with Alzheimer's disease. In some embodiments, the human patient has experienced a sustained clinical response as a result of receiving a combination of bupropion and dextromethorphan, wherein a sustained clinical response comprises a 30% or greater improvement from baseline in the human patients Cohen-Mansfield Agitation Inventory (CMAI) total score which is maintained for at least 4 consecutive weeks.

Some embodiments include a method of treating agitation associated with Alzheimer's disease (AD) and/or delaying time to relapse of Alzheimer's disease agitation versus placebo to a human being with a combination of dextromethorphan and bupropion, comprising: orally administering to a patient, once a day or twice a day, a dosage form containing a combination of 105 mg of bupropion hydrochloride, or a molar equivalent amount of the free base or another salt form of bupropion, and 45 mg of dextromethorphan hydrobromide, or a molar equivalent amount of the free base or another salt form of dextromethorphan. In some embodiments, the human patient has experienced a sustained clinical response as a result of receiving a combination of bupropion and dextromethorphan, wherein a sustained clinical response comprises a 30% or greater improvement from baseline in the human patients Cohen-Mansfield Agitation Inventory (CMAI) total score which is maintained for at least 4 consecutive weeks.

Some embodiments include a method of treating a human patient having agitation associated with Alzheimer's disease by administering a combination of dextromethorphan and bupropion, comprising orally administering to the human patient, once a day or twice a day, a dosage form comprising: 105 mg bupropion hydrochloride, or a molar equivalent amount of the free base or another salt form of bupropion, and 45 mg of dextromethorphan hydrobromide, or a molar equivalent amount of the free base or another salt form of dextromethorphan.

Some embodiments include a method of reducing relapse of agitation in Alzheimer's disease by administering a combination of dextromethorphan and bupropion, comprising orally administering to the human patient, once a day or twice a day, a dosage form comprising: 105 mg bupropion hydrochloride, or a molar equivalent amount of the free base or another salt form of bupropion, and 45 mg of dextromethorphan hydrobromide, or a molar equivalent amount of the free base or another salt form of dextromethorphan.

Some embodiments include a method of maintaining a clinical response in a human patient having agitation associated with Alzheimer's disease comprising orally administering a dosage form twice a day to the human patient, wherein the human patient has experienced a sustained clinical response as a result of receiving a combination of bupropion and dextromethorphan, wherein a sustained clinical response comprises a 30% or greater improvement from baseline in the human patients Cohen-Mansfield Agitation Inventory (CMAI) total score which is maintained for at least 4 consecutive weeks, wherein the dosage form comprises: 105 mg bupropion hydrochloride, or a molar equivalent amount of the free base or another salt form of bupropion, and 45 mg of dextromethorphan hydrobromide, or a molar equivalent amount of the free base or another salt form of dextromethorphan. In some embodiments, a sustained clinical response further comprises maintaining a Patient Global Impression of Change (PGI-C) score of 3 or less for at least 4 consecutive weeks.

Some embodiments include a method of reducing relapse of agitation in Alzheimer's disease comprising orally administering a dosage form twice a day to the human patient, wherein the human patient has experienced a sustained clinical response as a result of receiving a combination of bupropion and dextromethorphan, wherein a sustained clinical response comprises a 30% or greater improvement from baseline in the human patients Cohen-Mansfield Agitation Inventory (CMAI) total score which is maintained for at least 4 consecutive weeks, wherein the dosage form comprises: 105 mg bupropion hydrochloride, or a molar equivalent amount of the free base or another salt form of bupropion, and 45 mg of dextromethorphan hydrobromide, or a molar equivalent amount of the free base or another salt form of dextromethorphan.

Some embodiments include a method of treating agitation associated with Alzheimer's disease (AD) to a human patient, wherein oral administration of the subject combination to the human patient results in a rapid improvement in Alzheimer's disease agitation.

Some embodiments include a method of treating agitation associated with Alzheimer's disease (AD) to a human patient, wherein the percentage of human patients with agitation relapse is lower with administration of the subject combination than taking a placebo.

Some embodiments include a method of treating agitation associated with Alzheimer's disease (AD) to a human patient, wherein oral administration of the subject combination to the human patient delays the time to relapse of agitation symptoms as compared to a placebo.

Some embodiments include a method of treating agitation associated with Alzheimer's disease (AD) to a human patient, wherein oral administration of the subject combination to the human patient delays the time to relapse of agitation symptoms as compared to a placebo with about 3.6-fold lower risk of relapse.

Some embodiments include a method of treating agitation associated with Alzheimer's disease (AD) to a human patient, wherein oral administration of the subject combination to the human patient prevents relapse of Alzheimer's disease agitation (ADA) versus placebo.

BRIEF DESCRIPTION OF THE DRAWINGS

FIG. 1 depicts the ACCORD randomized discontinuation study design for the subject combination of dextromethorphan and bupropion (45 mg DM/105 mg BUP).[a] Sustained response of ≥30% improvement from baseline in the CMAI total score and improvement on the PGI-C (score 3) that were both maintained for ≥4 consecutive weeks.[b] Agitation relapse defined as a ≥10-point worsening in the CMAI total score from randomization or a CMAI total score greater than that at study entry; or hospitalization or other institutionalization due to ADA. AD=Alzheimer's disease; ADA=Alzheimer's disease-related agitation; BID=twice daily; BL=baseline; BUP=bupropion; CMAI=Cohen-Mansfield Agitation Inventory; DM=dextromethorphan; PGI-C=Patient Global Impression of Change.

FIG. 2A depicts the open-label period CMAI mean change from baseline over time for the subject combination of dextromethorphan and bupropion (45 mg DM/105 mg BUP). ***P<0.001 for change from baseline, paired t-test at each time point.

FIG. 2B depicts the open-label period participants with CMAI response over time for the subject combination of dextromethorphan and bupropion (45 mg DM/105 mg BUP).[a] CMAI response defined as ≥30% reduction from baseline. CMAI, Cohen-Mansfield Agitation Inventory.

FIG. 3A depicts the double-blind period probability of agitation relapse-free survival over time for the subject combination of dextromethorphan and bupropion (45 mg DM/105 mg BUP) compared with placebo.

FIG. 3B depicts the double-blind period probability of relapse incidence for the subject combination of dextromethorphan and bupropion (45 mg DM/105 mg BUP) compared with placebo.[a] Agitation relapse defined as a ≥10-point worsening (increase) in the CMAI total score from randomization or a CMAI total score greater than that at study entry for 2 consecutive weeks. CMAI=Cohen-Mansfield Agitation Inventory; mITT=modified intent-to-treat.

DETAILED DESCRIPTION

As mentioned above, this disclosure relates to administration of a combination of: 1) about 100-110 mg, about 104-106 mg, or about 105 mg of bupropion hydrochloride, or a molar equivalent amount of the free base form or another salt form of bupropion; and 2) about 40-50 mg, about 44-46 mg, or about 45 mg of dextromethorphan hydrobromide, or a molar equivalent amount of the free base form or another salt form of dextromethorphan. This combination is referred to for convenience herein as the "subject combination." In every instance where the subject combination is referred to herein, the combination of 105 mg of bupropion hydrochloride, or a molar equivalent amount of another salt form or the free base form of bupropion, and 45 mg of dextromethorphan hydrobromide, or a molar equivalent amount of another salt form or the free base form of dextromethorphan, is specifically contemplated.

Dextromethorphan hydrobromide is an uncompetitive NMDA receptor antagonist and a sigma-1 receptor agonist.

The chemical name of dextromethorphan hydrobromide is morphinan, 3-methoxy-17-methyl-, (9α,13α,14α), hydrobromide monohydrate. Dextromethorphan hydrobromide has the empirical formula $C_{18}H_{25}NO \cdot HBr \cdot H_2O$ and a molecular weight of 370.33. The structural formula is:

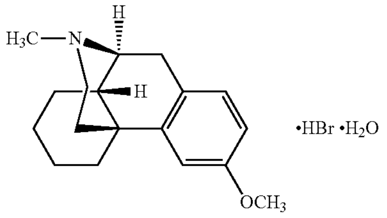 [SMILES: COc1ccc2c(c1)[C@]13CCCC[C@@H]1[C@H](C2)N(C)CC3]

Dextromethorphan hydrobromide powder is white or almost white, crystalline, and sparingly soluble in water.

Bupropion hydrochloride is an aminoketone and a CYP450 2D6 inhibitor.

The chemical name of bupropion hydrochloride is: (±)-1-(3-chlorophenyl)-2-[(1,1-dimethylethyl)amino]-1-propanone hydrochloride. Bupropion hydrochloride has the empirical formula $C_{13}H_{18}ClNO \cdot HCl$ and a molecular weight of 276.2. The structural formula is:

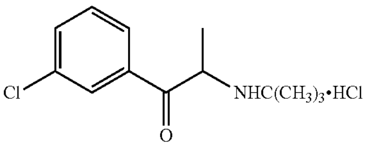

Bupropion hydrochloride powder is white and highly soluble in water.

The subject combination may be contained in an oral dosage form, including a tablet, such as an extended-release tablet. In some embodiments, the subject combination is contained in a dosage form for oral administration and is available as round bilayer tablets.

In some embodiments, each tablet containing the subject combination contains 45 mg of dextromethorphan hydrobromide in an immediate-release formulation. In some embodiments, each tablet of the subject combination contains 105 mg of bupropion hydrochloride in an extended-release formulation. In some embodiments, each tablet of the subject combination contains 45 mg of dextromethorphan hydrobromide in an immediate-release formulation and 105 mg of bupropion hydrochloride in an extended-release formulation.

In some embodiments, a tablet containing the subject combination contains L-cysteine hydrochloride monohydrate. In some embodiments, a tablet containing the subject combination contains carbomer homopolymer. In some embodiments, a tablet containing the subject combination contains microcrystalline cellulose. In some embodiments, a tablet containing the subject combination contains colloidal silicon dioxide. In some embodiments, a tablet containing the subject combination contains crospovidone. In some embodiments, a tablet containing the subject combination contains stearic acid. In some embodiments, a tablet containing the subject combination contains magnesium stearate.

In some embodiments, a tablet containing the subject combination contains the following inactive ingredients: L-cysteine hydrochloride monohydrate, carbomer homopolymer, microcrystalline cellulose, colloidal silicon dioxide, crospovidone, stearic acid, and magnesium stearate.

In some embodiments, the dosage is one tablet (or one dosage form containing 45 mg of dextromethorphan hydrobromide and 105 mg of bupropion hydrochloride) twice daily, e.g., given at least 8 hours apart. In some embodiments, no more than two doses containing 45 mg of dextromethorphan hydrobromide and 105 mg of bupropion hydrochloride are administered in the same day.

The subject combination may be administered orally with or without food. In some embodiments, the tablets are swallowed whole, and not crushed, divided, or chewed.

In the subject combination, bupropion inhibits the metabolism of dextromethorphan via CYP2D6. Dextromethorphan, when co-administered with bupropion, displays nonlinear pharmacokinetics at steady state, with greater than dose-proportional changes in AUC and $C_{max}$ for varying doses of dextromethorphan (30 to 60 mg) and less than dose-proportional changes for varying doses of bupropion (75 to 150 mg).

Steady state plasma concentrations of dextromethorphan and bupropion when given as the subject combination are achieved within 8 days. The accumulation ratios for dextromethorphan at steady state are about 20 and about 32, respectively based on $C_{max}$ and $AUC_{0-12}$. The accumulation ratios for bupropion at steady state are 1.1 and 1.5, respectively based on $C_{max}$ and $AUC_{0-12}$.

After administration of the subject combination, the median $T_{max}$ of dextromethorphan is about 3 hours and the median $T_{max}$ of bupropion is about 2 hours. The $C_{max}$ of hydroxybupropion metabolite occurs approximately 3 hours post-dose and is approximately 14 times the peak level of bupropion. The $AUC_{0-12}$ hydroxybupropion is about 19 times that of bupropion. The $C_{max}$ of the erythrohydroxybupropion and threohydroxybupropion metabolites occurs approximately 4 hours post-dose and is approximately equal to and about 5 times that of bupropion, respectively. The $AUC_{0-12}$ values of erythrohydroxybupropion and threohydroxybupropion are about 1.2 and about 7 times that of bupropion, respectively.

The subject combination can be taken with or without food. Dextromethorphan $C_{max}$ and $AUC_{0-12}$ were unchanged and decreased by 14%, respectively, and bupropion $C_{max}$ and $AUC_{0-12}$ were increased by 3% and 6%, respectively, when the subject combination was administered with food.

The plasma protein binding of dextromethorphan is approximately 60-70% and bupropion is 84%. The extent of protein binding of the hydroxybupropion metabolite is similar to that for bupropion; whereas the extent of protein binding of the threohydroxybupropion metabolite is about half that seen with bupropion.

Following 8 days of administration of the subject combination in extensive metabolizers, the mean elimination half-life of dextromethorphan was increased approximately 3-fold to about 22 hours, as compared to dextromethorphan given without bupropion.

The mean elimination half-life of dextromethorphan and bupropion was 22 hours and 15 hours, respectively. The apparent elimination half-life of hydroxybupropion, erythrohydroxybupropion and threohydroxybupropion metabolites were approximately 35, 44 and 33 hours, respectively.

Unlike the combination of quinidine and dextromethorphan, at a dose of a combination of 105 mg of bupropion hydrochloride and 45 mg of dextromethorphan hydrobromide given twice a day, the subject combination does not prolong the QT interval to any clinically relevant extent. Thus, for a human patient who is experiencing agitation associated with Alzheimer's disease and is at risk of QT prolongation and torsades de pointes, electrocardiographic evaluation of QT interval is not typically conducted on the human patient.

In addition to agitation associated with Alzheimer's disease, the subject combination may be used to treat other diseases in conditions in the patient populations or circumstances described herein. For example, the subject combination may be used to treat pain or a neurological disorder. Examples of neurological disorders that may be treated with the subject combination include, but are not limited to: affective disorders, psychiatric disorders, cerebral function disorders, movement disorders, dementias, motor neuron diseases, neurodegenerative diseases, seizure disorders, and headaches.

Affective disorders that may be treated by the subject combination include, but are not limited to, depression, major depression, treatment resistant depression, treatment resistant bipolar depression, bipolar disorders including cyclothymia, seasonal affective disorder, mood disorders, chronic depression (dysthymia), psychotic depression, postpartum depression, premenstrual dysphoric disorder (PMDD), situational depression, atypical depression, mania, anxiety disorders, attention deficit disorder (ADD), attention deficit disorder with hyperactivity (ADDH), and attention deficit/hyperactivity disorder (AD/HD), bipolar and manic conditions, obsessive-compulsive disorder, bulimia, obesity or weight-gain, narcolepsy, chronic fatigue syndrome, premenstrual syndrome, substance addiction or abuse, nicotine addiction, psycho-sexual dysfunction, pseudobulbar affect, and emotional lability.

Depression may be manifested by depressive symptoms. These symptoms may include psychological changes such as changes in mood, feelings of intense sadness, despair, mental slowing, loss of concentration, pessimistic worry, agitation, anxiety, irritability, guilt, anger, feelings of worthlessness, reckless behavior, suicidal thoughts, or attempts, and/or self-deprecation. Physical symptoms of depression may include insomnia, anorexia, appetite loss, weight loss, weight gain, decreased energy and libido, fatigue, restlessness, aches, pains, headaches, cramps, digestive issues, and/or abnormal hormonal circadian rhythms.

Psychiatric disorders that may be treated by the subject combination, include, but are not limited to, anxiety disorders, including but not limited to, phobias, generalized anxiety disorder, social anxiety disorder, panic disorder, agoraphobia, obsessive-compulsive disorder, and post-traumatic stress disorder (PTSD); mania, manic depressive illness, hypomania, unipolar depression, depression, stress disorders, somatoform disorders, personality disorders, psychosis, schizophrenia, delusional disorder, schizoaffective disorder, schizotypy, aggression, aggression in Alzheimer's disease, agitation, and agitation in Alzheimer's disease. Alzheimer's disease may also be referred to as dementia of the Alzheimer's type. Other neurobehavioral symptoms of Alzheimer's disease that may be treated include disinhibition and apathy.

Agitation in Alzheimer's disease occurs as the disease progresses. Agitation may present itself as inappropriate verbal, emotional, and/or physical behaviors. Inappropriate behaviors may include, but are not limited to, incoherent babbling, inappropriate emotional response, demands for attention, threats, irritability, frustration, screaming, repetitive questions, mood swings, cursing, abusive language, physical outbursts, emotional distress, restlessness, shredding, sleeping disturbances, delusions, hallucinations, pacing, wandering, searching, rummaging, repetitive body motions, hoarding, shadowing, hitting, scratching, biting, combativeness, hyperactivity, and/or kicking.

Alzheimer's disease (AD) is a progressive neurodegenerative disorder characterized by cognitive decline, and behavioral and psychological symptoms including agitation. AD is the most common form of dementia and afflicts an estimated 6 million individuals in the United States, a number that is anticipated to increase to approximately 14 million by 2050. Agitation is reported in up to 70% of patients with AD and is characterized by emotional distress, aggressive behaviors, disruptive irritability, and disinhibition. Managing agitation is a priority in AD. Agitation in patients with AD has been associated with increased caregiver burden, decreased functioning, accelerated cognitive decline, earlier nursing home placement, and increased mortality. There are currently no therapies approved by the FDA for the treatment of agitation in patients with AD.

Neurobehavioral symptoms have been known to appear during dementia and may be treated by the combination. Caregivers or families may feel more overwhelmed by patients' behavioral/psychological symptoms than by their cognitive impairment. Common forms of the syndrome are Alzheimer's disease, vascular dementia, dementia with Lewy bodies (abnormal aggregates of protein that develop inside nerve cells), and a group of diseases that contribute to frontotemporal dementia (degeneration of the frontal lobe of the brain). The symptoms that dementia patients have are similar to those of psychiatric disorders, but some are slightly different from each other. Neurobehavioral symptoms associated with dementia include depression, apathy, agitation, disinhibition, hallucinations, delusions, psychosis, impulsiveness, aggressiveness, compulsion, excessive sex drive, and personality disorders. Neurobehavioral symptoms such as disinhibition may also be found in other conditions such as traumatic brain injury.

Agitation in patients with Alzheimer's disease may be assessed using the Cohen Mansfield Agitation Inventory or CMAI. The CMAI assesses various behaviors including, hitting (including self), kicking, grabbing onto people, pushing, throwing things, biting, scratching, spitting, hurting self or others, tearing things or destroying property, making physical sexual advances, pacing, aimless wandering, inappropriate dress or disrobing, trying to get to a different place, intentional falling, eating/drinking inappropriate substances, handling things inappropriately, hiding things, hoarding things, performing repetitive mannerisms, general restlessness, screaming, making verbal sexual advances, cursing or verbal aggression, repetitive sentences or questions, strange noises (weird laughter or crying), complaining, negativism, constant unwarranted request for attention or help.

Schizophrenia may be treated by the combination including positive symptoms and/or negative symptoms of schizophrenia, or residual symptoms of schizophrenia. Other conditions that may treated include intermittent explosive disorder.

Cerebral function disorders that may be treated by the subject combination include, but are not limited to, disorders involving intellectual deficits such as senile dementia, Alzheimer's type dementia, memory loss, amnesia/amnestic syndrome, epilepsy, disturbances of consciousness, coma, lowering of attention, speech disorders, voice spasms, Parkinson's disease, Lennox-Gastaut syndrome, autism, hyperkinetic syndrome, and schizophrenia. Cerebral function disorders also include disorders caused by cerebrovascular diseases including, but not limited to, stroke, cerebral infarction, cerebral bleeding, cerebral arteriosclerosis, cerebral venous thrombosis, head injuries, and the like where symptoms include disturbance of consciousness, senile dementia, coma, lowering of attention, and speech disorders.

Substance addiction abuse that may be treated by the subject combination includes, but is not limited to, drug dependence, addiction to cocaine, psychostimulants (e.g., crack, cocaine, speed, meth), nicotine, alcohol, opioids, anxiolytic and hypnotic drugs, cannabis (marijuana), amphetamines, hallucinogens, phencyclidine, volatile solvents, and volatile nitrites. Nicotine addiction includes nicotine addiction of all known forms, such as smoking cigarettes, cigars and/or pipes, e-cigarettes or vaping, and addiction to chewing tobacco.

Movement disorders that may be treated by the subject combination include, but are not limited to, akathisia, akinesia, associated movements, athetosis, ataxia, ballismus, hemiballismus, bradykinesia, cerebral palsy, chorea, Huntington's disease, Huntington's disease chorea, rheumatic chorea, Sydenham's chorea, dyskinesia, tardive dyskinesia, dystonia, blepharospasm, spasmodic torticollis, dopamine-responsive dystonia, Parkinson's disease, restless legs syndrome (RLS), tremor, essential tremor, and Tourette's syndrome, and Wilson's disease.

Dementias that may be treated by the subject combination include, but are not limited to, Alzheimer's disease, Parkinson's disease, vascular dementia, dementia with Lewy bodies, mixed dementia, fronto-temporal dementia, Creutzfeldt-Jakob disease, normal pressure hydrocephalus, Huntington's disease, Wernicke-Korsakoff Syndrome, and Pick's disease.

Motor neuron diseases that may be treated by the subject combination include, but are not limited to, amyotrophic lateral sclerosis (ALS), progressive bulbar palsy, primary lateral sclerosis (PLS), progressive muscular atrophy, post-polio syndrome (PPS), spinal muscular atrophy (SMA), spinal motor atrophies, Tay-Sach's disease, Sandhoff disease, and hereditary spastic paraplegia.

Neurodegenerative diseases that may be treated by the subject combination include, but are not limited to, Alzheimer's disease, prion-related diseases, cerebellar ataxia, spinocerebellar ataxia (SCA), spinal muscular atrophy (SMA), bulbar muscular atrophy, Friedrich's ataxia, Huntington's disease, Lewy body disease, Parkinson's disease, amyotrophic lateral sclerosis (ALS or Lou Gehrig's disease), multiple sclerosis (MS), multiple system atrophy, Shy-Drager syndrome, corticobasal degeneration, progressive supranuclear palsy, Wilson's disease, Menkes disease, adrenoleukodystrophy, cerebral autosomal dominant arteriopathy with subcortical infarcts and leukoencephalopathy (CADASIL), muscular dystrophies, Charcot-Marie-Tooth disease (CMT), familial spastic paraparesis, neurofibromatosis, olivopontine cerebellar atrophy or degeneration, striatonigral degeneration, Guillain-Barré syndrome, and spastic paraplesia.

Seizure disorders that may be treated by the subject combination include, but are not limited to, epileptic seizures, nonepileptic seizures, epilepsy, febrile seizures; partial seizures including, but not limited to, simple partial seizures, Jacksonian seizures, complex partial seizures, and epilepsia partialis continua; generalized seizures including, but not limited to, generalized tonic-clonic seizures, absence seizures, atonic seizures, myoclonic seizures, juvenile myoclonic seizures, and infantile spasms; and status epilepticus.

Types of headaches that may be treated by the subject combination include, but are not limited to, migraine, tension, and cluster headaches.

Other neurological disorders that may be treated by the subject combination include, Rett Syndrome, autism, tinnitus, disturbances of consciousness disorders, sexual dysfunction, intractable coughing, narcolepsy, cataplexy; voice disorders due to uncontrolled laryngeal muscle spasms, including, but not limited to, abductor spasmodic dysphonia, adductor spasmodic dysphonia, muscular tension dysphonia, and vocal tremor; diabetic neuropathy, chemotherapy-induced neurotoxicity, such as methotrexate neurotoxicity; incontinence including, but not limited, stress urinary incontinence, urge urinary incontinence, and fecal incontinence; and erectile dysfunction.

In some embodiments, the subject combination may be used to treat pain, joint pain, pain associated with sickle cell disease, pseudobulbar affect, depression (including treatment resistant depression), disorders related to memory and cognition, schizophrenia, Parkinson's disease, amyotrophic lateral sclerosis (ALS), Rhett's syndrome, seizures, cough (including chronic cough), etc.

In some embodiments, the subject combination may be administered orally to relieve musculoskeletal pain including low back pain, and pain associated with rheumatoid arthritis, juvenile rheumatoid arthritis, osteoarthritis, erosive osteoarthritis, sero-negative (non-rheumatoid) arthropathies, non-articular rheumatism, peri-articular disorders, axial spondyloarthritis including ankylosing spondylitis, Paget's disease, fibrous dysplasia, SAPHO syndrome, transient osteoarthritis of the hip, vertebral crush fractures, osteoporosis, etc.

In some embodiments, the subject combination may be administered to relieve inflammatory pain including musculoskeletal pain, arthritis pain, and complex regional pain syndrome.

Arthritis refers to inflammatory joint diseases that can be associated with pain. Examples of arthritis pain include pain associated with osteoarthritis, erosive osteoarthritis, rheumatoid arthritis, juvenile rheumatoid arthritis, sero-negative (non-rheumatoid) arthropathies, non-articular rheumatism, peri-articular disorders, neuropathic arthropathies including Charcot's foot, axial spondyloarthritis including ankylosing spondylitis, and SAPHO syndrome.

In some embodiments, the subject combination is used to treat chronic musculoskeletal pain.

In some embodiments, the subject composition may be administered to relieve complex regional pain syndrome, such as complex regional pain syndrome type I (CRPS-I), complex regional pain syndrome type II (CRPS-II), CRPS-NOS, or another type of CRPS. CRPS is a type of inflammatory pain. CRPS can also have a neuropathic component. Complex regional pain syndrome is a debilitating pain syndrome. It is characterized by severe pain in a limb that can be accompanied by edema, and autonomic, motor, and sensory changes.

In some embodiments, the subject composition may be administered orally to relieve neuropathic pain.

Examples of neuropathic pain include pain due to diabetic peripheral neuropathy or diabetic peripheral neuropathic pain, post-herpetic neuralgia, trigeminal neuralgia, monoradiculopathies, phantom limb pain, central pain, pain due to multiple sclerosis, etc. Other causes of neuropathic pain include cancer-related pain, lumbar nerve root compression, spinal cord injury, post-stroke pain, central multiple sclerosis pain, HIV-associated neuropathy, and radio- or chemotherapy associated neuropathy, etc.

In some embodiments, the subject composition may be administered to relieve fibromyalgia.

The term "treating" or "treatment" includes the diagnosis, cure, mitigation, treatment, or prevention of disease in man or other animals, or any activity that otherwise affects the structure or any function of the body of man or other animals.

In some embodiments, the subject combination may reduce CMAI (Cohen-Mansfield Agitation Inventory) total score by at least 5, about 5-10, about 10-15, about 15-20, about 20-25, about 25-30, or about 30-35, or any value bounded by or in between these ranges from baseline after administering the subject combination orally to a human patient for 1 week, 2 weeks, 3 weeks, 4 weeks, 5 weeks, 6 weeks, 7 weeks, 8 weeks, or 9 weeks.

In some embodiments, after a sustained clinical response is achieved as a result of receiving a combination of bupropion and dextromethorphan, wherein a sustained clinical response comprises a 30% or greater improvement from baseline in the human patients Cohen-Mansfield Agitation Inventory (CMAI) total score which is maintained for at least 4 consecutive weeks, the subject combination is administered twice a day for at least 1 week, at least 2 weeks, at least 3 weeks, at least 4 weeks, at least 2 months, at least 3 months, at least 4 months, at least 5 months, at least 6 months, at least 7 months, at least 8 months, at least 9 months, at least 10 months, at least 11 months, at least 12 months, at least 18 months, at least 2 years, up to 1 year, up to 2 years, up to 3 years, up to 4 years, up to 5 years, up to 10 years, or longer.

In some embodiments, the percentage of human patients with CMAI response, or the likelihood of a CMAI response, (defined as ≥30% reduction from baseline) may be at least 20%, about 20-40%, about 40-60%, about 60-80%, about 80-90%, about 90-95%, about 80-100%, about 40%, about 50-55%, about 60%, about 70%, about 60-70%, about 70-80%, about 22%, about 54%, about 61%, about 79%, about 91%, about 93%, about 95%, or any value bounded by or in between these ranges after administering the subject combination orally to a human patient for 1 week, 2 weeks, 3 weeks, 4 weeks, 5 weeks, 6 weeks, 7 weeks, 8 weeks, or 9 weeks.

Agitation relapse is defined as a ≥10-point worsening (increase) in a CMAI total score that is greater than that at study entry for 2 consecutive weeks. In some embodiments, the probability (%) of agitation relapse-free survival in human patients with the treatment of the subject combination may be higher than taking a placebo. In some embodiments, the probability (%) of agitation relapse-free survival with the treatment of the subject combination may be at least 80%, at least 85%, at least 90%, about 90-95%, about 95-100%, about 90-92%, about 92-94%, about 94-96%, about 96-98%, or any value bounded by or in between these ranges after administering the subject combination orally to a human patient for about 1 week, about 2 weeks, about 3 weeks, about 4 weeks, about 5 weeks, about 6 weeks, about 7 weeks, about 10 weeks, about 11 weeks, about 12 weeks, about 13 weeks, about 14 weeks, about 15 weeks, about 16 weeks, about 15-20 weeks, about 20 weeks, about 20-25 weeks, about 25 weeks, about 26 weeks, or longer. In some embodiments, the risk of relapse was about at least 2-fold, at least 3-fold, 3-4 fold, about 3-fold, about 4-fold, about 3.6-fold, or about 4-5 fold lower with the subject combination compared with a placebo.

In some embodiments, the percentage of human patients with agitation relapse may be substantially lower with the treatment of the subject combination than placebo. In some embodiments, the percentage of human patients with agitation relapse may be very low, such as less than 10%, about 5-10%, about 5%, about 5-6%, about 5-8%, about 7.5%, about 6-8%, or about 7-8%.

In some embodiments, the subject combination may substantially delay the time to relapse of agitation symptoms as compared to placebo. In some embodiment, the subject combination may delay the time to relapse of agitation symptoms as compared to placebo with about 2-fold, about 3-fold, about 4-fold, about 3-4 folds, about 4-5 fold, or about 3.6-fold lower risk of relapse compared to placebo.

In some embodiments, the subject combination may significantly prevent relapse of Alzheimer's disease agitation (ADA) versus placebo.

In some embodiments, treatment with the subject combination may result in a rapid and substantial improvement in Alzheimer's disease agitation.

A subject combination may be used to treat any disease or condition identified as treatable by the combination of bupropion and dextromethorphan in any of the following U.S. Pat. Nos. 8,569,328, 9,168,234, 9,189,905 9,205,083, 9,238,032, 9,278,095, 9,314,462, 9,370,513, 9,375,429, 9,408,815, 9,421,176, 9,457,023, 9,457,025, 9,474,731, 9,486,450, 9,700,528, 9,700,553, 9,707,191, 9,763,932, 9,861,595, 9,867,819, 9,968,568, 10,058,518, 10,064,857, 10,080,727, 10,092,560, 10,092,561, 10,105,327, 10,105,361, 10,251,879, 10,463,634, 10,512,643, 10,548,857, 10,596,167, 10,772,850, 10,780,064, 10,780,066, 10,786,469, 10,786,496, 10,799,497, 10,806,710, 10,864,209, 10,874,663, 10,874,664, 10,874,665, 10,881,624, 10,881,657, 10,894,046, 10,894,047, 10,898,453, all of which are incorporated by reference herein in their entireties for their disclosure of diseases that may be treated by a combination of bupropion and dextromethorphan, including specific embodiments and combinations described therein.

Example 1

Efficacy and Safety of DM/BUP (Dextromethorphan-Bupropion) in Agitation Associated with Alzheimer's Disease: Results from ACCORD, a Phase 3, Double-Blind, Placebo-Controlled, Relapse Prevention Trial Dextromethorphan-bupropion, or DM/BUP, e.g., 45 mg dextromethorphan hydrobromide and 105 mg bupropion hydrochloride, is a novel, oral, investigational N-methyl-D-aspartate (NMDA) receptor antagonist with multimodal activity under development for the treatment of Alzheimer's disease (AD) agitation and other central nervous system (CNS) disorders.

DM/BUP utilizes a proprietary formulation and dose of dextromethorphan and bupropion, and Axsome's metabolic inhibition technology, to modulate the delivery of the components. The dextromethorphan component of DM/BUP is an uncompetitive NMDA receptor antagonist, also known as a glutamate receptor modulator, and a sigma-1 receptor agonist. The bupropion component of DM/BUP serves to increase the bioavailability of dextromethorphan, and is a norepinephrine and dopamine reuptake inhibitor.

The DM/BUP tablets are prepared for oral administration. They are round bilayer tablets. Each tablet contains 45 mg dextromethorphan hydrobromide (equivalent to 32.98 mg of the dextromethorphan free base) in an immediate-release formulation and 105 mg bupropion hydrochloride (equivalent to 91.14 mg of the bupropion free base) in an extended-release formulation. Each tablet contains the following inactive ingredients: carbomer homopolymer, colloidal silicon dioxide, crospovidone, glyceryl monocaprylocaprate, L-cysteine hydrochloride monohydrate, magnesium stearate, microcrystalline cellulose, polyvinyl alcohol, red iron oxide, sodium lauryl sulfate, stearic acid, talc, titanium dioxide, and/or yellow iron oxide.

Introduction

Alzheimer's disease (AD) is the most common cause of dementia, affecting 6.7 million Americans in 2023, which is projected to rise to 13.8 million by 2060 due to population aging. AD-related agitation (ADA) is reported in up to 70% of people with AD and is characterized by emotional distress, aggressive behaviors, disruptive irritability and disinhibition. ADA and other behavioral symptoms are associated with increased caregiver burden, decreased functioning, accelerated cognitive decline, earlier nursing home placement, and increased mortality. Nonpharmacological therapies for ADA are not always effective and the only US Food and Drug Administration (FDA)-approved treatment for agitation in dementia due to AD is brexpiprazole, an antipsychotic with a box warning for use in dementia-related psychosis due to increased risk of death.

DM/BUP (dextromethorphan-bupropion, extended-release tablet]) is a novel, oral, N-methyl-D-aspartate (NMDA) receptor antagonist and sigma-1 receptor agonist approved by the FDA for the treatment of major depressive disorder in adults. Imbalances in neurotransmitters in people with AD contribute to agitation, and these neurotransmitters may be modulated by DM/BUP treatment.

Methods & Study Design

The Key inclusion and exclusion criteria for the study enrolled participants with probable AD and clinically significant agitation are shown in Table 1.

TABLE 1

Key inclusion and exclusion criteria

| Inclusion | Exclusion |
|---|---|
| Age 65-90 years (inclusive) | Predominantly non-AD dementia Agitation symptoms not secondary to AD |
| Probable AD according to 2011 NIA-AA criteria | Concurrent medical condition that may interfere with study conduct |
| Clinically significant agitation according to IPA provisional definition | Medically inappropriate in opinion of investigator |
| MMSE score 10-24 (inclusive) | |
| Caregiver participation | |

Note:
AD, Alzheimer's disease;
IPA, International Psychogeriatric Association;
MMSE, Mini Mental State Examination;
NIA-AA, National Institute of Aging-Alzheimer Association The ACCORD (Assessing Clinical Outcomes in Alzheimer's Disease Agitation; NCT04797715) study was a Phase 3, randomized, discontinuation, double-blind, placebo-controlled trial, multi-center trial to evaluate the efficacy and safety of DM/BUP in patients with Alzheimer's disease agitation (ADA) for the treatment of ADA (FIG. 1). Patients with a diagnosis of probable Alzheimer's disease and clinically meaningful agitation associated with their disease were enrolled into a 9-week, open-label period, during which they were treated with DM/BUP and monitored for a sustained clinical response. Sustained clinical response was defined as a ≥30% improvement from baseline in the Cohen-Mansfield Agitation Inventory (CMAI) total score and improvement on the PGI-C (score of 3) that are both maintained for at least 4 consecutive weeks.

Patients who experienced a sustained clinical response during the open-label treatment period were then randomized in a 1:1 ratio, to continue treatment with DM/BUP or to switch to placebo treatment, in a double-blind fashion for up to 26 weeks. Treatment was continued until either a relapse of agitation symptoms or the end of the 26-week double-blind period, whichever occurred first. Relapse was defined as a ≥10-point worsening in the CMAI total score from randomization or a CMAI total score greater than that at study entry; or hospitalization or other institutionalization due to agitation associated with Alzheimer's disease.

A total of 178 patients were enrolled into the open-label period and treated with DM/BUP, and 108 patients were randomized to continue on DM/BUP (n=53) or to switch to placebo (n=55). The mean Cohen-Mansfield Agitation Inventory (CMAI) total score at baseline study entry was 70.9. The mean CMAI total scores at randomization were 43.7 (DM/BUP) and 44.9 (placebo). The minimum score on the CMAI is 29, corresponding to the total absence of symptoms, with higher scores corresponding to greater agitation.

The primary endpoint in the study was time from randomization to relapse of Alzheimer's disease agitation (in the double-blind period) calculated by the Kaplan-Meier estimates and the hazard ratio. The key secondary endpoint, to assess relapse prevention, was the percentage of patients who relapsed. The primary timepoint for open-label efficacy assessments was Week 5 and the key secondary timepoint was Week 2. P-values for the open-label period were calculated versus baseline.

In FIG. 1, AD represents Alzheimer's disease; ADA represents Alzheimer's disease-related agitation; BID represents twice daily; BL represents baseline; BUP represents bupropion; CMAI represents Cohen-Mansfield Agitation Inventory; DM represents dextromethorphan; and PGI-C represents Patient Global Impression of Change.

Patient Population

Participants had moderate severity AD dementia according to Mini Mental State Examination (MMSE). Baseline demographics and clinical characteristics were similar between groups in the double-blind period (Table 2). In the double-blind period, 54.2% of participants completed the study, and termination of the study by the sponsor was the most common cause of discontinuation (22.4%).

TABLE 2

| Demographics and baseline characteristics | Open-Label Period (Safety Population) | Double-Blind Period (ITT Population) | |
|---|---|---|---|
| | DM/BUP (n = 178) | DM/BUP (n = 53) | Placebo (n = 55) |
| Demographics | | | |
| Age, years, mean (SD) | 74.9 (6.0) | 74.1 (6.0) | 74.9 (6.2) |
| Women, n (%) | 95 (53.4) | 27 (50.9) | 30 (54.5) |
| Race, n (%) | | | |
| White | 152 (85.4) | 45 (84.9) | 47 (85.5) |
| Black | 18 (10.1) | 4 (7.5) | 7 (12.7) |
| Asian | 4 (2.2) | 2 (3.8) | 1 (1.8) |
| Other or not reported | 4 (2.2) | 2 (3.8) | 0 |
| Clinical characteristics | | | |
| CMAI total score, mean (SD) | 70.9 (22.3) | 43.7 (10.2) | 44.9 (10.9) |
| NPI-AA total score, mean (SD)[a] | 7.0 (2.0) | 4.1 (2.0) | 3.6 (1.9) |
| CGI-S agitation, mean (SD) | 4.3 (0.6) | 2.7 (0.8) | 2.9 (0.8) |
| MMSE total score, mean (SD) | 17.8 (4.0) | 17.8 (4.8) | 18.5 (4.4) |

[a]NPI-AA total score n = 49 participants in both DM/BUP and placebo groups in the double-blind period. CGI-S, Clinical Global Impression-Severity; CMAI, Cohen-Mansfield Agitation Inventory; ITT, intent-to-treat; MMSE, Mini Mental state examination; NPI-AA, Neuropsychiatric Inventory-Agitation and Aggression domain.

Efficacy in Open-Label Prior to Randomized Discontinuation

A total of 178 patients were treated with open-label DM/BUP for up to 9 weeks and assessed for efficacy. The primary timepoint for open-label efficacy assessments was 5 weeks, and the key secondary timepoint was 2 weeks. P-values were calculated versus baseline. The mean CMAI total score was 70.9 at baseline.

The open-label period CMAI mean change from baseline and participants with CMAI response are shown in FIGS. 2A and 2B. In FIG. 2A, P<0.001 for change from baseline, paired t-test at each time point. CMAI represents Cohen-Mansfield Agitation Inventory, and CMAI response is defined as ≥30% reduction from baseline.

As shown in FIGS. 2A and 2B, during the open-label period, there was statistically significant improvement in Cohen-Mansfield Agitation Inventory total score at all timepoints, as early as week 1 (FIG. 2A), with increasing response rate over time (FIG. 2B). The more detailed open-label Period Results are summarized below.

Treatment with DM/BUP was associated with a mean reduction from baseline in the CMAI total score of 6.7 points at Week 1, 11.0 points at Week 2, and 20.6 points at Week 5 (p<0.001 for all) (FIG. 2A).

Clinical response on the CMAI (defined as ≥30% reduction from baseline) after treatment with DM/BUP was achieved by 21.8% of patients at Week 1, 40.4% of patients at Week 2, and 70.0% of patients at Week 5 (FIG. 2B).

Treatment with DM/BUP was also associated with improvements on all CMAI subscales including the Physically Aggressive subscale at all timepoints (p<0.001).

Improvement in Alzheimer's disease agitation, assessed using the clinician rated mADCS-CGIC, was achieved by 47.1% of patients at Week 1, 66.3% of patients at Week 2, and 86.3% of patients at Week 5, after treatment with DM/BUP.

Improvement in Alzheimer's disease agitation, assessed using the caregiver rated PGI-C, was achieved by 51.2% of patients at Week 1, 67.5% of patients at Week 2, and 89.3% of patients at Week 5, after treatment with DM/BUP.

Caregiver distress, assessed using the NPI Agitation and Aggression Caregiver Distress score, was significantly reduced after treatment with DM/BUP (p<0.001, at Weeks 4 and 8).

Caregiver burden, assessed using the ZBI, was significantly reduced after treatment with DM/BUP (p=0.006 at Week 4, p=0.003 at Week 8).

Patient quality of life, assessed using the caregiver rated QoL-AD scale, was significantly improved after treatment with DM/BUP (p<0.001 at Week 4, p=0.013 at Week 8).

Depressive symptoms, assessed using the CSDD, were significantly reduced after treatment with DM/BUP ($p<0.001$, at Weeks 4 and 8).

Efficacy in the Double-Blind Period

A total of 108 patients were randomized, 53 to continued treatment with DM/BUP, and 55 switched to placebo. The mean CMAI total scores at randomization were 43.7 and 44.9 for the DM/BUP and placebo groups respectively.

The double-blind period probability of agitation relapse-free survival and relapse incidence are shown in FIG. 3A and FIG. 3B. In FIG. 3A or 3B, Agitation relapse is defined as a ≥10-point worsening (increase) in the CMAI total score from randomization or a CMAI total score greater than that at study entry for 2 consecutive weeks. CMAI represents Cohen-Mansfield Agitation Inventory; and mITT represents modified intent-to-treat.

As shown in FIG. 3A and FIG. 3B, DM/BUP met the primary endpoint by substantially and statistically increased the time to relapse of agitation symptoms compared with placebo (Hazard ratio, 0.275, P=0.014) (FIG. 3A). The risk of relapse was 3.6-fold lower with DM/BUP compared with placebo.

DM/BUP also met the key secondary endpoint by significantly preventing relapse of Alzheimer's disease agitation as compared with placebo (7.5% vs 25.9% of participants respectively, p=0.018) (FIG. 3B).

The rates of adverse events in the double-blind period were 28.3% in the DM/BUP group and 22.2% in the placebo group. Discontinuations in the double-blind period due to adverse events were low (0% for DM/BUP and 1.9% for placebo).

Safety

The treatment-emergent adverse events are summarized in Table 3. There were no sedation treatment-emergent adverse events with DM/BUP. No clinically significant cardiovascular changes were observed with DM/BUP. There was no evidence of cognitive decline in participants treated with DM/BUP according to the MMSE (mean change from baseline to week 8 in open-label period, 0.4; P=0.421). No deaths occurred in the DM/BUP group during any period.

TABLE 3

Summary of treatment-emergent adverse events

| n (%) | Open-Label Period (Safety Population) DM/BUP (n = 178) | Double-Blind Period (Safety Population) DM/BUP (n = 53) | Double-Blind Period (Safety Population) Placebo (n = 54) |
|---|---|---|---|
| Participant with ≥1 TEAE | 65 (36.5) | 15 (28.3) | 12 (22.2) |
| Serious TEAE | 1 (0.6) | 1 (1.9) | 2 (3.7) |
| Drug-related TEAE | 38 (21.3) | 3 (5.7) | 2 (3.7) |
| Participant with TEAE leading to | | | |
| Study discontinuation | 7 (3.9) | 0 | 1 (1.9) |
| Death | 0 | 0 | 1 (1.9)[a] |
| Most common TEAE (≥5% in any group)[b] | | | |
| Dizziness | 17 (9.6) | 0 | 1 (1.9) |
| Diarrhea | 8 (4.5) | 4 (7.5) | 2 (3.7) |
| Fall | 9 (5.1) | 4 (7.5) | 1 (1.9) |
| Back pain | 2 (1.1) | 3 (5.7) | 2 (3.7) |

[a]Death due to cardiac arrest;

[b]TEAEs reported by preferred term. TEAE, treatment-emergent adverse event.

One serious adverse event was reported in the DM/BUP group (faecaloma), which was determined by the investigator to be not related to study medication, and 2 serious adverse events were reported in the placebo group (cardiac arrest, femur fracture). Falls were reported in 4 patients in the DM/BUP group, none of which were associated with serious adverse events and all of which were determined by the investigators to be not related to study medication, and in 2 patients in the placebo group, one of which was associated with a femur fracture. One death was reported in the placebo group. There was no evidence of cognitive decline for patients treated with DM/BUP as shown by the Mini-Mental State Examination (MMSE), a widely utilized measure of general cognitive function. Treatment with DM/BUP was not associated with sedation.

CONCLUSIONS

DM/BUP significantly increased the time to relapse of agitation symptoms compared with placebo in the double-blind period.

Improvement of agitation symptoms with DM/BUP was rapid and durable in the initial open-label period.

Overall, DM/BUP was generally well tolerated with no new safety signals identified from the prior phase 2 trial.

No sedation treatment-emergent adverse events, clinically significant cardiovascular changes, or evidence of cognitive decline were observed in participants treated with DM/BUP in this study.

Thus, DM/BUP is a promising candidate for the treatment of agitation in patients with Alzheimer's disease.

Additionally, rapid and substantial improvement in Alzheimer's disease agitation was reported by both clinicians and caregivers on global measures. Clinicians reported improvement in agitation in 66.3% of patients at Week 2 and 86.3% at Week 5 after treatment with DM/BUP, as assessed using the modified Alzheimer's Disease Cooperative Study-Clinical Global Impression of Change for Agitation (mADCS-CGIC). Caregivers reported improvement in agitation in 67.5% of patients at Week 2 and 89.3% at Week 5 after treatment with DM/BUP, as assessed using the Patient Global Impression of Change (PGI-C) rated by the caregiver.

Caregiver distress and burden, patient quality of life, and depressive symptoms were all statistically significantly improved compared to baseline after patients were treated with open-label DM/BUP. Caregiver distress was assessed using the NPI Agitation and Aggression Caregiver Distress score ($p<0.001$, at Weeks 4 and 8). Caregiver burden was assessed using the Zarit Burden Interview (ZBI) (p=0.006 at Week 4, p=0.003 at Week 8). Patient quality of life was assessed using the caregiver rated Quality of Life Alzheimer's Disease (QoL-AD) scale ($p<0.001$ at Week 4, p=0.013 at Week 8). Depressive symptoms were assessed using the Cornell Scale for Depression in Dementia (CSDD) ($p<0.001$, at Weeks 4 and 8).

To conclude, DM/BUP statistically significantly delayed time to relapse of Alzheimer's disease agitation versus placebo (p=0.014, primary endpoint), statistically significantly reduced relapse of Alzheimer's disease agitation versus placebo (p=0.018, key secondary endpoint), and statistically significant improvement in Alzheimer's disease agitation, as measured by the CMAI total score, starting at Week 1 with open-label DM/BUP ($p<0.001$ vs baseline, all timepoints). Improvement in Alzheimer's disease agitation, assessed by the modified Alzheimer's Disease Cooperative Study-CGIC scale, achieved by 66% of patients at 2 weeks and 86% at 5 weeks. Improvement in Alzheimer's disease agitation, assessed by the PGI-C scale, achieved by 68% of patients at 2 weeks and 89% at 5 weeks.

Jeffrey Cummings, MD, ScD, Director Emeritus of the Cleveland Clinic Lou Ruvo Center for Brain Health, and Chambers Professor of Brain Science at the University of Nevada Las Vegas said, "Agitation is one of the most troubling and consequential aspects of Alzheimer's disease for patients and their caregivers as it is associated with early nursing home placement, accelerated cognitive decline, and increased mortality. The results of the ACCORD trial demonstrate convincing clinical activity for DM/BUP on agitation associated with Alzheimer's disease based on both a significant delay in symptom relapse as well as a reduction of relapse compared to placebo. Treatment with [DM/BUP] during the open-label period in a large cohort of patients resulted in rapid and clinically meaningful improvements in Alzheimer's disease agitation. The improvements were especially notable since they were seen on the aggressive symptom subscales of the agitation measures. Agitation occurs in the majority of patients with Alzheimer's disease and there are currently no treatments approved for this condition. [DM/BUP] could potentially fill this high unmet medical need for patients and their caregivers, if approved, based on the observed positive efficacy and favorable safety and tolerability results."

Unless otherwise indicated, all numbers expressing quantities of ingredients, properties such as amounts, percentage, and so forth used in the specification and claims are to be understood in all instances as indicating both the exact values as shown and as being modified by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Use of the term "comprising" or "comprises" herein also contemplates that use of "consisting essentially of," "consists essentially of," "consisting of," or "consists of" in its place.

Affirmative recitation of an element anywhere herein should be understood to contemplate both including and excluding that element.

The terms "a," "an," "the" and similar referents used in the context of describing the embodiments (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the embodiments and does not pose a limitation on the scope of any claim. No language in the specification should be construed as indicating any non-claimed element essential to the practice of the claims.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from a group, for reasons of convenience and/or to expedite prosecution. When any such inclusion or deletion occurs, the specification is deemed to contain the group as modified thus fulfilling the written description of all Markush groups if used in the appended claims.

Certain embodiments are described herein, including the best mode known to the inventors for carrying out the claimed embodiments. Of course, variations on these described embodiments will become apparent to those of ordinary skill in the art upon reading the foregoing description. The inventor expects skilled artisans to employ such variations as appropriate, and the inventors intend for the claimed embodiments to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

The invention claimed is:

1. A method of maintaining a clinical response in the treatment of agitation associated with Alzheimer's disease in a human patient, comprising orally administering a dosage form twice a day to the human patient, wherein the human patient has experienced a sustained clinical response as a result of receiving a combination of bupropion and dextromethorphan, wherein a sustained clinical response comprises a 30% or greater improvement from baseline in the human patient's Cohen-Mansfield Agitation Inventory (CMAI) total score which is maintained for at least 4 consecutive weeks, and maintaining a Patient Global Impression of Change (PGI-C) score of 3 or less for at least 4 consecutive weeks, and wherein the dosage form comprises: about 105 mg bupropion hydrochloride, or a molar equivalent amount of the free base or another salt form of bupropion, and about 45 mg of dextromethorphan hydrobromide, or a molar equivalent amount of the free base or another salt form of dextromethorphan.

2. A method of reducing relapse of agitation in Alzheimer's disease in a human patient comprising orally administering a dosage form twice a day to the human patient, wherein the human patient has experienced a sustained clinical response as a result of receiving the dosage form, wherein a sustained clinical response comprises a 30% or greater improvement from baseline in the human patients Cohen-Mansfield Agitation Inventory (CMAI) total score which is maintained for at least 4 consecutive weeks, wherein the dosage form comprises: about 105 mg bupropion hydrochloride, or a molar equivalent amount of the free base or another salt form of bupropion, and about 45 mg of dextromethorphan hydrobromide, or a molar equivalent amount of the free base or another salt form of dextromethorphan.

3. The method of claim 1, wherein the dosage form comprising about 105 mg of bupropion hydrochloride and about 45 mg of dextromethorphan hydrobromide is orally administered twice a day to the human patient.

4. The method of claim 1, wherein the dosage form is administered twice a day for at least 4 weeks.

5. The method of claim 1, wherein the dosage form is administered twice a day for at least 3 months.

6. The method of claim 1, wherein the dosage form is administered twice a day for at least 6 months.

7. The method of claim 1, wherein the dosage form is a solid dosage form.

8. The method of claim 7, wherein the solid dosage form further contains a carbomer homopolymer, colloidal silicon dioxide, crospovidone, glyceryl monocaprylocaprate, L-cysteine hydrochloride monohydrate, magnesium stearate, microcrystalline cellulose, polyvinyl alcohol, red iron oxide, sodium lauryl sulfate, stearic acid, talc, titanium dioxide, yellow iron oxide, or a combination thereof.

9. The method of claim 7, wherein the solid dosage form is a tablet.

10. The method of claim 9, wherein the tablet is a bilayer tablet.

11. The method of claim 1, wherein dextromethorphan hydrobromide is in an immediate-release formulation.

12. The method of claim 1, wherein bupropion hydrochloride is in an extended-release formulation.

13. The method of claim 11, wherein bupropion hydrochloride is in an extended-release formulation.

14. The method of claim 1, wherein oral administration of the dosage form to the human patient results in a rapid improvement in agitation associated with Alzheimer's disease.

15. The method of claim 2, wherein the dosage form comprising about 105 mg of bupropion hydrochloride and about 45 mg of dextromethorphan hydrobromide is orally administered twice a day to the human patient.

16. The method of claim 2, wherein the dosage form is administered twice a day for at least 4 weeks.

17. The method of claim 2, wherein the dosage form is administered twice a day for at least 3 months.

18. The method of claim 2, wherein the dosage form is administered twice a day for at least 6 months.

19. The method of claim 2, wherein the dosage form is a solid dosage form.

20. The method of claim 19, wherein the solid dosage form further contains a carbomer homopolymer, colloidal silicon dioxide, crospovidone, glyceryl monocaprylocaprate, L-cysteine hydrochloride monohydrate, magnesium stearate, microcrystalline cellulose, polyvinyl alcohol, red iron oxide, sodium lauryl sulfate, stearic acid, talc, titanium dioxide, yellow iron oxide, or a combination thereof.

21. The method of claim 19, wherein the solid dosage form is a tablet.

22. The method of claim 21, wherein the tablet is a bilayer tablet.

23. The method of claim 2, wherein dextromethorphan hydrobromide is in an immediate-release formulation.

24. The method of claim 2, wherein bupropion hydrochloride is in an extended-release formulation.

25. The method of claim 23, wherein bupropion hydrochloride is in an extended-release formulation.

26. The method of claim 2, wherein the percentage of human patients with agitation relapse is lower with administration of the dosage form than taking a placebo.

27. The method of claim 2, wherein oral administration of the dosage form to the human patient delays the time to relapse of agitation symptoms as compared to a placebo.

28. The method of claim 2, wherein oral administration of the dosage form to the human patient delays the time to relapse of agitation symptoms as compared to a placebo with about 3.6-fold lower risk of relapse.

29. The method of claim 2, wherein oral administration of the dosage form to the human patient reduces the risk of relapse of agitation in Alzheimer's disease as compared to a placebo.

* * * * *